(12) United States Patent
Jozefiak et al.

(10) Patent No.: US 7,754,200 B2
(45) Date of Patent: Jul. 13, 2010

(54) PHOSPHATE TRANSPORT INHIBITORS

(75) Inventors: Thomas H. Jozefiak, Watertown, MA (US); Cecilia M. Bastos, South Grafton, MA (US); Chad C. Huval, Somerville, MA (US)

(73) Assignee: Genzyme Corporation, Waltham, MA (US)

( * ) Notice: Subject to any disclaimer, the term of this patent is extended or adjusted under 35 U.S.C. 154(b) by 838 days.

(21) Appl. No.: 11/438,679

(22) Filed: May 22, 2006

(65) Prior Publication Data
US 2006/0280719 A1 Dec. 14, 2006

Related U.S. Application Data

(62) Division of application No. 10/392,280, filed on Mar. 19, 2003, now Pat. No. 7,109,184.

(60) Provisional application No. 60/365,940, filed on Mar. 19, 2002.

(51) Int. Cl.
*A61K 31/74* (2006.01)
(52) U.S. Cl. ..................... 424/78.17; 525/188
(58) Field of Classification Search .................. 514/89; 515/102; 424/17.17; 525/188
See application file for complete search history.

(56) References Cited

U.S. PATENT DOCUMENTS

| | | | |
|---|---|---|---|
| 3,632,634 A | 1/1972 | Maier | |
| 3,845,169 A | 10/1974 | Maier et al. | |
| 4,806,532 A | 2/1989 | Dousa | |
| 5,374,628 A * | 12/1994 | Biller | 514/95 |
| 5,496,545 A | 3/1996 | Holmes-Farley et al. | |
| 5,508,342 A * | 4/1996 | Antonucci et al. | 524/788 |
| 5,574,024 A | 11/1996 | Ebetino | |
| 5,618,851 A * | 4/1997 | Trochimcznk et al. | 521/34 |
| 5,667,775 A | 9/1997 | Holmes-Farley et al. | |
| 6,083,495 A | 7/2000 | Holmes-Farley et al. | |
| 7,109,184 B2 | 9/2006 | Jozefiak et al. | |

FOREIGN PATENT DOCUMENTS

| | | |
|---|---|---|
| EP | 0 401 705 A2 | 12/1990 |
| EP | 563730 * | 10/1993 |
| EP | 0 570 706 A1 | 11/1993 |
| EP | 1 485 391 B1 | 8/2006 |
| GB | 2 227 663 A | 8/1990 |
| WO | WO 94/20508 | 9/1994 |
| WO | WO 03/080630 A2 | 10/2003 |

OTHER PUBLICATIONS

Magnin, D.R., et al., "1,1-Bisphosphonate Squalene Synthase Inhibitors: Interplay Between the Isoprenoid Subunit and the Diphosphate Surrogate," *J. Med. Chem.*, 38:2596-2605 (1995).
McKenna, C.E., et al., "α-Halo [(Phenylphosphinyl)methyl]phosphonates as Specific Inhibitors of Na+-Gradient-Dependent Na+-Phosphate Cotransport across Renal Brush Border Membrane," *J. Med. Chem.*, 35:4885-4892 (1992).
Ebetino, F.H., et al., "Recent Work on The Synthesis of Phosphonate-Containing, Bone-Active Heterocycles," *Heterocycles*, 30(2):855-862 (1990).
Kelley, J.L., et al., "[[(Guaninylalkyl)phosphinico]methyl]phosphonic Acids. Multisubstrate Analogue Inhibitors of Human Erythrocyte Purine Nucleoside Phosphorylase," *J. Med. Chem.*, 38:1005-1014 (1995).
Stowell, M.H.B., et al., "The Phosphonylphosphinyl Dianion: A Convenient Synthon For The Preparation Of Biologically Interesting Phosphonylphosphinyl (P-C-P-C-) Compounds," *Tetrahedron Lett.*, 30(4):411-414 (1989).
Biller, S.A., and Forster, C., "The Synthesis of Isoprenoid (Phosphinylmethyl) Phosphonates," *Tetrahedron*, 46(19):6645-6658 (1990).
Biller, S.A., et al., "Isoprenoid (Phosphinylmethyl) phosphonates as Inhibitors of Squalene Synthetase," *J. Med. Chem.*, 31(10):1869-1871 (1988).

(Continued)

*Primary Examiner*—Jafar Parsa
*Assistant Examiner*—Chukwuma O Nwaonicha
(74) *Attorney, Agent, or Firm*—Hamilton, Brook, Smith, Reynolds, P.C.

(57) ABSTRACT

Disclosed is a phosphate transport inhibiting compound represented by Structural Formula (I):

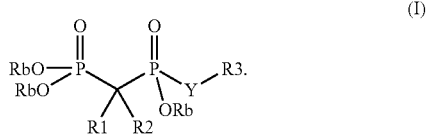

R1 and R2 are independently —H, an electron withdrawing group or a $C_1$-$C_{10}$ alkyl group.

Y is a covalent bond, a substituted methylene group, an unsubstituted methylene group or —CR1R2P(O)(OH)—.

R3 is a hydrocarbyl group optionally comprising one or more amine, ammonium, ether, thioether or phenylene linking groups, a substituted hydrocarbyl group optionally comprising one or more amine, ammonium, ether, thioether or phenylene linking groups, a heteroaryl group, a substituted heteroaryl group or a phenyl group substituted with one or more groups selected from —Cl, —Br, —F, —CN, —NO$_2$, —OR$^a$, —N(R$^a$)$_2$, —COOR$^a$, —CON(R$^a$)$_2$, —COR$^a$, —S(O)R$^a$, —S(O)$_2$R$^a$, —S(O)$_2$N(R$^a$)$_2$, —NR$^a$S(O)$_2$R$^a$, —NR$^a$-COR$^a$, a halogenated lower alkyl group, an aryl group, a substituted aryl group, or a halogenated alkoxy group.

Each R$^a$ is independently —H, lower alkyl, substituted lower alkyl, aryl or substituted aryl.

Each Rb is independently —H, a lower alkyl group, or a phosphate protecting group.

19 Claims, No Drawings

OTHER PUBLICATIONS

Flohr, A., et al., "α-Functionalized Phosphonylphosphinates: Synthesis and Evaluation as Transcarbamoylase Inhibitors," *J. Med. Chem.*, 42:2633-2640 (1999).

McClard, R. W., et al., "Novel Phosphonylphosphinyl (P-C-P-C) Analogues of Biochemically Interesting Diphosphates. Syntheses and Properties of P-C-P-C Analogues of Isopentenyl Disphospate and Dimethylallyl Diphosphate," *J. Am. Chem. Soc.*, 109:5544-5545 (1987).

Lindell, S. D., and Turner, R. M., "Synthesis of Potential Inhibitors of the Enzyme Aspartate Transcarbomylase," *Tetrahedron Lett.*, 31(37):5381-5384 (1990).

Hilfiker, Helene, et al., "Characterization of a Murine Type II Sodium-Phosphate Contransporter Expressed in Mammalian Small Intestine," *Proc. Natl. Acad. Sci., USA*, 95:14564-14569 (1998).

Ullrich, K. J., "Renal Transporters for Organic Anions and Organic Anions and Organic Cations. Structural Requirements for Substrates," *J. Membrane Biol.*, 158:95-107 (1997).

Loghman-Adham, M., et al., "Inhibition of $Na^+$-$P_i$ Cotransporter in Small Gut Brush Border by Phosphonocarboxylic Acids," *Am. J. Physiol.*, 252:G245-G249 (1987).

Loghman-Adham, M., "Use of Phosphonocarboxylic Acids as Inhibitors of Sodium-Phosphate Cotransport," *Gen. Pharmac.*, 272(2):305-312 (1996).

Rassier, M.E., et al., "A Novel Specific Inhibitor and Probe of $Na^+$-$P_i$ Cotransporter of Renal Cortical Brush Border Membrane Vesicles (BBMV)," *J. Am. Soc. Nephrol.*, 1(4):581 (1990).

McKenna, C.E., et al., "Synthesis and HIV-1 Reverse Transcriptase Inhibition Activity of Functionalized Pyrophosphate Analogues," *Phosphorous, Sulfur, and Silicon*, 76:139-142 (1993).

Maynard, H.D., et al., "Synthesis of Norbornenyl Polymers with Bioactive Oligopeptides by Ring-Opening Metathesis Polymerization," *Macromolecules*, 33(17):6239-6248 (2000).

Bielawski, C.W., et al., "Highly Efficient Ring-Opening Metathesis Polymerization (ROMP) Using New Ruthenium Catalysts Containing N-Heterocyclic Carbene Ligands," *Angew. Chem. Int. Ed.*, 39(16):2903-2906 (2000).

Sundell, M.J., et al., "Synthesis and Use as a Catalyst of Porous Polystyrene with Bis(phosphonic acid)-Functionalized Surfaces[1]," *Chem. Mater.*, 5:372-376 (1993).

Sundell, M.J., et al., "Preparation of Poly[ethylene-g-(vinylbenzyl chloride)] and Functionalization with Bis(phosphonic acid) Derivatives," *Reactive Polymers*, 25:1-16 (1995).

Ullrich, K.J., et al., "Interaction of Alkyl/Arylphosphonates, Phosphonocarboxylates and Diphosphonates with Different Anion Transport Systems in the Proximal Renal Tubule," *J. Pharmacol. Exp. Ther.*, 283(3):1223-1229 (1997).

Szczepanska-Konkel, M., et al., "Structural Requirement of Monophosphates for Inhibition of $Na^+$-$P_i$ Cotransport in Renal Brush Border Membrane," *Biochem. Pharmacol.*, 38(23):4191-4197 (1989).

\* cited by examiner

PHOSPHATE TRANSPORT INHIBITORS

RELATED APPLICATION

This application is a Divisional of U.S. application Ser. No. 10/392,280, filed Mar. 19, 2003 now U.S. Pat. No. 7,109,184, which claims the benefit of U.S. Provisional Application No. 60/365,940, filed on Mar. 19, 2002. The entire teachings of the above application are incorporated herein by reference.

BACKGROUND OF THE INVENTION

People with inadequate renal function, hypoparathyroidism, or certain other medical conditions often have hyperphosphatemia, or elevated serum phosphate levels (over 6 mg/dL). Hyperphosphatemia, especially if present over extended periods of time, leads to severe abnormalities in calcium and phosphorus metabolism, often manifested by hyperparathyroidism, bone disease and calcification in joints, lungs, eyes and vasculature. For patients who exhibit renal insufficiency, elevation of serum phosphorus within the normal range has been associated with progression of renal failure and increased risk of cardiovascular events. The progression of kidney disease can be slowed by reducing phosphate retention. Thus, for renal failure patients who are hyperphosphatemic and for chronic kidney disease patients whose serum phosphate is within the normal range or is only slightly elevated, therapy to reduce phosphate retention is beneficial.

For patients experiencing hyperphosphatemia, calcium salts have been widely used to bind intestinal phosphate and prevent its absorption. Different types of calcium salts including calcium carbonate, acetate, citrate, alginate, and ketoacid salts have been utilized for phosphate binding. The major problem with all of these therapeutics is the hypercalcemia which often results from absorption of high amounts of ingested calcium. Hypercalcemia causes serious side effects such as cardiac arrhythmias, renal failure, and skin and visceral calcification. Frequent monitoring of serum calcium levels is required during therapy with calcium-based phosphate binders. Other calcium and aluminum-free phosphate binders have drawbacks including the amount and frequency of dosing required to be therapeutically active.

An alternative approach to the prevention of phosphate absorption from the intestine in patients with elevated phosphate serum levels is through inhibition of the intestinal transport system, which mediates phosphate uptake in the intestine. It is understood that phosphate absorption in the upper intestine is mediated at least in part by a carrier-mediated mechanism that couples the absorption of phosphate to that of sodium in an energy-dependent fashion. Inhibition of intestinal phosphate transport will reduce serum phosphate levels. This would be particularly advantageous in patients susceptible to hyperphosphatemia as a result of renal insufficiency or in patients that have a disease that is treatable by inhibiting the uptake of phosphate from the intestines. Inhibition of phosphate reabsorption from the urine by the kidneys would also be advantageous for treating chronic renal failure. Furthermore, inhibition of phosphate transport may slow the progression of renal failure and reduce risk of cardiovascular events.

SUMMARY OF THE INVENTION

It has now been found that certain phosphinyl phosphonate compounds are effective inhibitors of phosphate transport proteins. For example, phosphinyl phosphonate compounds shown in Table 1 inhibit phosphate transport, many with an $IC_{50}$ below 50 µM, in an in vitro rabbit intestinal Brush Border Membrane assay (see Example 28). Based on this discovery, methods of treating a subject with chronic kidney disease, a disease associated with disorders of phosphate metabolism or a disease mediated by impaired phosphate-transport function are disclosed. Also, novel phosphate transport inhibiting polymers and compounds are disclosed.

One embodiment of the present invention is a phosphate transport inhibiting compound represented by Structural Formula (I):

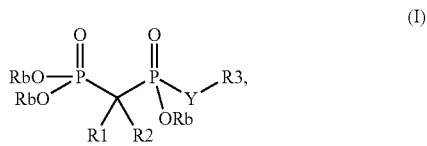

or a pharmaceutically acceptable salt or a prodrug thereof.

R1 and R2 are independently —H, an electron withdrawing group or a $C_1$-$C_{10}$ alkyl group. Preferably, R1 and R2 are independently —H or —F.

Y is a covalent bond, a substituted methylene group, an unsubstituted methylene group, or —CR1R2P(O)(OH)—. Preferably, Y is a covalent bond or —CHX—, wherein X is —H, —F or a lower alkyl group. Y can also be —$CX_2$—, where X is —H, —F or a lower alkyl group, preferably —F.

R3 is a hydrocarbyl group optionally comprising one or more amine, ammonium, ether, thioether or phenylene linking groups, a substituted hydrocarbyl group optionally comprising one or more amine, ammonium, ether, thioether or phenylene linking groups, a heteroaryl group, a substituted heteroaryl group or a phenyl group substituted with one or more groups selected from —Cl, —Br, —F, —CN, —$NO_2$, —$OR^a$, —O(halogenated lower alkyl) such as —$OCF_3$, —$N(R^a)_2$, —$COOR^a$, —$CON(R^a)_2$, —$COR^a$, —$S(O)R^a$, —$S(O)_2R^a$, —$S(O)_2N(R^a)_2$, —$NR^aS(O)_2R^a$, —$NR^aCOR^a$, a halogenated lower alkyl group, (e.g., $CF_3$), a halogenated alkoxy group, an aryl group or a substituted aryl group.

Each $R^a$ is independently —H, lower alkyl, substituted lower alkyl, aryl or substituted aryl.

Each Rb is independently —H, lower alkyl or a phosphate protecting group. Preferably, Rb is —H.

Another embodiment of the present invention is a method of inhibiting phosphate transport in a subject in need of phosphate transport inhibition. The method comprises the step of administering to the subject an effective amount of a compound represented by Structural Formula (I).

Another embodiment of the present invention is a polymer comprising one or more phosphinyl phosphonate groups. A polymer (or compound) comprising a phosphinyl phosphonate group is said to be "phosphinyl phosphonate functionalized". Preferably, the phosphinyl phosphonate group is represented by Structural Formula (II), (V) or (VI):

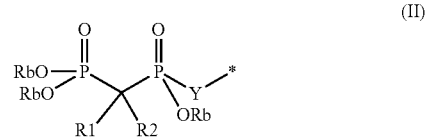

-continued

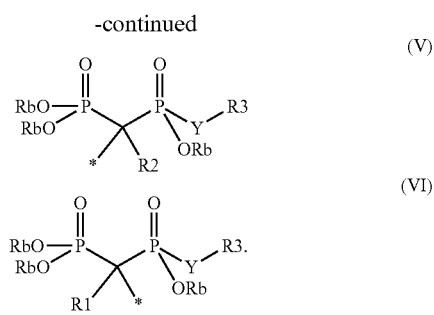

R1, R2, Rb and Y in Structural Formulas (II), (V) and (VI) are as described above for Structural Formula (I). Also included are esters (e.g., alkyl esters) of the phosphinyl phosphonate group represented by Structural Formulas (II), (V) and (VI).

Another embodiment of the present invention is a method of inhibiting phosphate transport in a subject in need of phosphate transport inhibition. The method comprises the step of administering to the subject an effective amount of a polymer comprising one or more pendant phosphinyl phosphonate groups.

The phosphate transport inhibitors disclosed herein can be used for the manufacture of a medicament for inhibiting phosphate transport in a subject in need of such treatment, e.g., for treating or preventing disorders of phosphate metabolism or impaired phosphate transport function such as hyperphosphatemia, hyperparathyroidism, uremic bone disease, soft tissue calcification (e.g., cardiovascular calcification), progression of renal failure, cardiovascular events and osteoporosis. The invention also relates to the disclosed phosphinyl phosphonate compounds and phosphinyl phosphonate functionalized polymers for use in inhibiting phosphate transport in a subject in need of such treatment, e.g., for treating or for preventing chronic renal failure or a disease associated with hyperphosphatemia.

Another embodiment of the present invention is a pharmaceutical composition comprising a phosphate transport inhibiting compound or polymer of the present invention and a pharmaceutically acceptable carrier, diluent or excipient. Pharmaceuticals compositions of the invention can be used in therapy, such as inhibiting phosphate transport in a subject in need of such treatment.

Another embodiment of the present invention is the use of a compound represented by Structural Formula (I) or a polymer comprising one or more pendant phosphinyl phosphate groups in combination with a pharmaceutically acceptable compound which binds phosphate (a "phosphate sequesterant"). The pharmaceutically acceptable phosphate binder can be a calcium, aluminum or lanthanum-containing phosphate binder or a phosphate-binding polymer such as those disclosed in U.S. Pat. Nos. 5,496,545, 5,667,775 and 6,083,495; the contents of which are incorporated herein by reference in their entirety. Preferably, the phosphate-binding polymer is a polyallylamine such as sevelamer (e.g, sevelamer hydrochloride, sevelamer carbonate, sevelamer bicarbonate).

The compounds and polymers disclosed herein are effective inhibitors of phosphate transport and thus are useful for treatment of hyperphosphatemia, chronic renal failure, diseases associated with disorders of phosphate metabolism and impaired phosphate transport function. The beneficial aspects on chronic renal failure, disorders of phosphate metabolism or impaired phosphate transport function, e.g., hyperparathyroidism, uremic bone disease, renal bone disease, soft tissue calcification (e.g., cardiovascular calcification), cardiovascular events, and osteoporosis, could be mediated by either an effect on the intestinal transporters or on transporters in other tissues, such as those present in bone, kidney or vasculature.

DETAILED DESCRIPTION OF THE INVENTION

Disclosed herein are small molecule and polymer inhibitors of phosphate transport. These compounds are preferably used to inhibit (i.e., reduce or prevent, in whole or in part) phosphate transport in the gastrointestinal tract and are therefore useful in treating conditions and diseases characterized by elevated phosphate levels, for example, hyperphosphatemia, renal failure and hypoparathyroidism. Many of the small molecule inhibitors are expected to be absorbed by the gastrointestinal tract and are therefore available systemically. As a consequence, they can inhibit phosphate transport in other organs such as the kidneys and can advantageously be used to treat chronic renal failure. The small molecule inhibitors are represented by Structural Formula (I) and comprise a phosphinyl phosphonate group. The polymer inhibitors also comprise phosphinyl phosphonate groups, which are pendent from or integral to the polymer backbone.

R1 and R2 in Structural Formulas (I) and (II) can be an electron withdrawing group. The methylene group represented by Y in Structural Formulas (I) and (II) can also be substituted with an electron withdrawing group.

In one preferred embodiment, Y in Structural Formulas (I), (II), (V) and (VI) is —CHX— and X is a lower alkyl group. When Y is —CHX— and X is a lower alkyl group, then R3 is preferably a hydrocarbyl group. The hydrocarbyl group represented by R3 can be an unsubstituted lower alkyl group or is alternatively substituted at the terminal position (referred to herein as "terminally substituted") with -M-CR4=CHR5, —N(R7)$_2$, —OR7, —COOR7, —Br, —Cl, —I or —N$^+$(R7)$_3$. M is —NR6-, —O—, —C(O)—, —C(O)O—, —C(O)NR6-, —NR6C(O)—, —(CH$_2$)$_q$—, or phenylene; R4 and R5 are independently —H or a C1-C5 alkyl group; each R6 is independently —H, lower alkyl, substituted lower alkyl, aryl or substituted aryl; each R7 is independently —H or C1-C3 lower alkyl group (preferably methyl); and q is 0 or 1. The hydrocarbyl group represented by R3 can comprise zero, one or more linking groups. The term "linking group" is defined below.

In another preferred embodiment, Y in Structural Formulas (I), (II), (IV), (V) and (VI) is —CHX— or —CX$_2$— and X is —H or —F. When Y is —CHX— and X is —H or —F, R3 has a number of suitable values. For example, R3 is preferably a hydrocarbyl group, more preferably an unsubstituted lower alkyl group, or alternatively a hydrocarbyl group that is terminally substituted with -M-CR4=CHR5, —N(R7)$_2$, —OR7, —COOR7, —Br, —Cl, —I, —N$^+$(R7)$_3$. M, R4-R5 and R7 are as described above. The hydrocarbyl group represented by R3 can comprise zero, one or more linking groups, which can be one, two, three, four or more atoms away from the phosphinyl moiety. The term "linking group" is defined below. In another alternative, R3 is a phenyl group substituted with one or more groups selected from —Cl, —Br, —F, —CN, —NO$_2$, —OR$^a$, —O(halogenated lower alkyl) such as —OCF$_3$, —N(R$^a$)$_2$, —COOR, —CON(R$^a$)$_2$, —COR$^a$, —S(O)R$^a$, —S(O)$_2$R$^a$, —S(O)$_2$N(R$^a$)$_2$, —NR$^a$S(O)$_2$R$^a$, —NR$^a$COR$^a$, a halogenated lower alkyl group (e.g., CF$_3$), an aryl group, or a substituted aryl group. R$^a$ is as defined above.

In another embodiment, Y in Structural Formulas (I), (V) and (VI) is a covalent bond, —CH$_2$—, —CHF—, —CF$_2$— and R3 is —(CH$_2$)$_m$—R8. R8 is a substituted or unsubstituted heteroaryl group or a substituted or unsubstituted phenyl group. When R8 is a substituted or unsubstituted heteroaryl group, m is an integer from 0 to 20, 2 to 20, 3 to 20, 4 to 20, 4 to 40, 6 to 20, 8 to 20 or 10 to 20. When R8 is a substituted or unsubstituted phenyl group, m is preferably an integer from 2 to 20, 3 to 20, 4 to 20, 4 to 40, 6 to 20, 8 to 20 or 10 to 20. When Y is —CHF— or —CF$_2$— and R8 is a substituted or unsubstituted phenyl group, m is preferably an integer from 0 to 20, 2 to 20, 4 to 20, 4 to 40, 6 to 20, 8 to 20 or 10 to 20.

In an especially preferred embodiment, Y in Structural Formulas (I), (V) and (VI) is a covalent bond, —CH$_2$—, —CHF— or —CF$_2$— and R3 is —(CH$_2$)$_p$—R14. p is an integer from 7 to 18 and R14 is —H or a terminal substituent, preferably —H.

In another embodiment, Y in Structural Formulas (I), (V) and (VI) is a covalent bond, —CH$_2$—, —CHF— or —CF$_2$— and R3 is represented by Structural Formula (III):

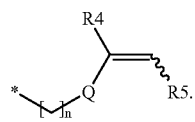

(III)

n is an integer from 1 to about 18; Q is a covalent bond, —CH$_2$—, 1,3-phenylene, 1,4-phenylene, —C(O)O—, —C(O)NR6-, —C(O)—, —O—, —NR6-, —CH$_2$NR6- or —CH$_2$O—; and R4-R6 are as described above. A covalent bond is one preferred value for Q. Another preferred value of Q is —C(O)NH—, i.e., an acrylamide monomer.

In another embodiment, Y in Structural Formula (I) is a substituted methylene group, or —CR1R2P(O)(OH)— when R3 is a hydrocarbyl group optionally comprising one or more amine, ammonium, ether, thioether or phenylene linking groups; a substituted hydrocarbyl group optionally comprising one or more amine, ammonium, ether, thioether or phenylene linking groups; a heteroaryl group; a substituted heteroaryl group; or a phenyl group substituted with one or more groups selected from —Cl, —Br, —F, —CN, —NO$_2$, —OR$^a$, —N(R$^a$)$_2$, —COOR, —CON(R$^a$)$_2$, —COR$^a$, —S(O)R$^a$, —S(O)$_2$R$^a$, —S(O)$_2$N(R$^a$)$_2$, —NR$^a$S(O)$_2$R$^a$, —NR$^a$COR$^a$, a halogenated lower alkyl group, an aryl group, a substituted aryl group, or a halogenated alkoxy group; or, preferably, Y in Structural Formula (I) is a covalent bond, or an unsubstituted methylene group and R3 is a C7-C18 saturated unsubstituted hydrocarbyl group, or a C7-C18 saturated monosubstituted hydrocarbyl group wherein the substituent is at the terminal position. R$^a$ is as defined above.

A polymer of the present invention is preferably represented by Structural Formula (IV):

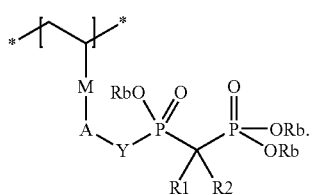

(IV)

M, R1, R2 and Y in Structural Formula (IV) are as described above; and A is an inert spacer group. The term "inert spacer group" is defined below. Preferably R1 and R2 are independently —H or —F and Y is a covalent bond, —CH$_2$—, —CHF— or —CF$_2$—. More preferably, R1 and R2 are independently —H or —F; Y is a coalent bond, —CH$_2$— or —CHF—; and A is a hydrocarbyl group optionally comprising one or more amine, ether, thioether, amide or ester linking groups.

Another polymer of the present invention is represented by Structural Formula (XIV), where the phosphinyl phosphonate group is part of the polymer backbone:

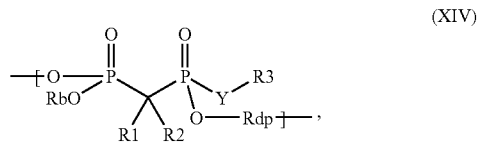

(XIV)

wherein each Rdp is independently a diol or polyol and the values of R1, R2, R3, Rb and Y (including the preferred values) are as defined above in Structural Formula (I). A diol has two hydroxyl group, while a polyol has three or more hydroxyl groups. Examples of diols and polyols include polyvinylalcohol, polallylalcohol, polyethylene glycol, polypropylene glycol, a polysaccharide, and a branched polysaccharide.

A "straight chained hydrocarbyl group" is an alkylene group, i.e., —(CH$_2$)$_x$— where x is a positive integer (e.g., from 1 to about 18), preferably between 1 and about 10, and more preferably between about 8 and about 14. The carbon chain of the straight chained hydrocarbyl group can be optionally interrupted with one or more linking groups. A "linking group" refers to a functional group which replaces a methylene in a straight chained hydrocarbyl group. Examples of suitable linking groups include an alkene, alkyne, phenylene, ether (—O—), thioether (—S—), amine (—N(R10)-), or ammonium (—N$^+$(R10R11)-). R10 and R11 are independently —H, alkyl, substituted alkyl, phenyl, substituted phenyl, or, taken together with the nitrogen atom to which they are bonded, a non-aromatic, nitrogen-containing heterocyclic group. Preferably, R10 and R10 are not both —H. More preferably, R10 and R11 are both alkyl groups and even more preferably, both methyl. R10 and R11 can be the same or different, but are preferably the same.

The terms "terminal position" or "terminus" refer to the methylene carbon of the straight chained hydrocarbyl group most distant from Y. Substituents at the terminal position of a straight chained hydrocarbyl group are referred to herein as "terminal substituents". Examples of terminal substituents include a cyclohexyl group, an oxirane group, a substituted or unsubstituted benzenesulfonamide group, a substituted or unsubstituted benzamide group, a propionamide group, an acrylamide group, a substituted or unsubstituted naphthamide group, a phthalimide group, a 1,2-dibromo-ethyl group, a 1-hydroxy-2-bromo-ethyl group, a substituted or unsubstituted phenyl group, a substituted or unsubstituted heteroaryl group, CH$_2$=CH—, -M-CR4=CHR5, —N(R7)$_2$, —OR7, —COOR7, —Br, —Cl, —I or —N$^+$(R7)$_3$. M, R4-R7 and q are as defined above.

A "substituted hydrocarbyl group" has one or more substituents bonded at one or more positions other than at the terminus. Suitable substituents are those which do not significantly lower the phosphate transport inhibiting ability of the compound or polymer, for example, do not lower either activity by more than a factor of about two. Examples of suitable substituents include C1-C3 straight chained or branched alkyl, C1-C3 straight chained or branched haloalkyl, —OH, halogen (—Br, —Cl, —I and —F), —O(C1-C3 straight chain or branched alkyl) or —O(C1-C3 straight chain or branched haloalkyl).

An "aliphatic group" is a straight chained, branched or cyclic non-aromatic hydrocarbon which is completely saturated or which contains one or more units of unsaturation. Typically, a straight chained or branched aliphatic group has from 1 to about 10 carbon atoms, preferably from 1 to about 4, and a cyclic aliphatic group has from 3 to about 10 carbon atoms, preferably from 3 to about 8. An aliphatic group is preferably a straight chained or branched alkyl group, e.g., methyl, ethyl, n-propyl, iso-propyl, n-butyl, sec-butyl, tert-butyl, pentyl, hexyl, heptyl or octyl, or a cycloalkyl group with 3 to about 8 carbon atoms. A C1-C4 straight chained or branched alkyl group or a C3-C8 cyclic alkyl group is also referred to as a "lower alkyl" group.

The term "aryl group" refers to carbocyclic aromatic groups such as phenyl, naphthyl, and anthracyl, and heteroaryl groups such as imidazolyl, isoimidazolyl, thienyl, furanyl, pyridyl, pyrimidyl, pyranyl, pyrazolyl, pyrrolyl, pyrazinyl, thiazoyl, isothiazolyl, oxazolyl, isooxazolyl, 1,2,3-trizaolyl, 1,2,4-triazolyl, and tetrazolyl.

Heteroaryl groups also include fused polycyclic aromatic ring systems in which a carbocyclic aromatic ring or heteroaryl ring is fused to one or more other heteroaryl rings. Examples include benzothienyl, benzofuranyl, indolyl, quinolinyl, benzothiazolyl, benzoisothiazolyl, benzooxazolyl, benzoisooxazolyl, benzimidazolyl, quinolinyl, isoquinolinyl and isoindolyl.

Suitable substituents for a substituted aliphatic group, a substituted aryl group a substituted hydrocarbyl group, a substituted alkyl group or a substituted heteroaryl group, are those which do not significantly lower the phosphate transport inhibiting activity of the compound or polymer (e.g., do not lower the activity by more than a factor of about two compared with the corresponding unsubstituted compound). Examples include —OH, a halogen (—Br, —Cl, —I and —F), —O(R12), —O—CO—(R12), —CN, —NO$_2$, —COOH, =O, —NH$_2$ —NH(R12), —N(R12)$_2$. —COO (R12), —CONH$_2$, —CONH(R12), —CON(R12)$_2$, —SH, —S(R12), an aliphatic group, an aryl group and a heteroaryl group. Each R12 is independently —H, an alkyl group or an aryl group. A substituted aliphatic group, a substituted aryl group a substituted hydrocarbyl group, a substituted alkyl group or a substituted heteroaryl group, can have more than one substituent.

The term "electron withdrawing group", as it is used herein, has the meaning commonly afforded the term in the art. Specifically, an electron withdrawing group is a substituent which results in a phenyl ring having less electron density when the group is present on the phenyl ring than when it is absent. Electron withdrawing groups have a Hammet sigma value greater than zero (see, for example, C. Hansch, A. Leo and D. Hoeckman, "Exploring QSAR Hydrophobic, Electronic and Steric Constants", American Chemical Society (1995), pages 217-232). Examples of electron withdrawing groups include halogens, —NO$_2$, —CN, —CF$_3$ and —OCF$_3$. Fluoride is a preferred electron withdrawing group.

Also included in the present invention are pharmaceutically acceptable salts of the compounds and polymers described herein. Compounds and polymers disclosed herein which possess a sufficiently acidic, a sufficiently basic functional groups or both, can react with any of a number of organic or inorganic base, and inorganic and organic acids, to form a salt. Phosphinyl phosphonates contain three acidic protons and therefore readily form salts in the presence of base.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like.

Acids commonly employed to form acid addition salts from compounds with basic groups are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

When the compound or polymer comprises an ammonium group such as —N$^+$(R7)$_3$ or —N$^+$(R10R11)-, a pharmaceutically acceptable counteranion is also present. Examples include chloride, bromide, iodide, nitrate, sulfate, carbonate, and the like. A compound or polymer can have more than one type of counteranion when the overall number of positive charges is greater than one.

Phosphinyl phosphonate groups can also form a salt with an appropriate, pharmaceutically acceptable polymer. Typically, such polymers contain basic groups, such as amine groups. Aliphatic amine polymers, such as polyallylamines (e.g., sevelamer) are advantageously used as counterions to a phosphinyl phosphonate group.

The term "polymer backbone" or "backbone" refers to that portion of the polymer which is a continuous chain, comprising the bonds which are formed between monomers upon polymerization. The composition of the polymer backbone can be described in terms of the identity of the monomers from which it is formed, without regard to the composition of branches, or side chains, off of the polymer backbone. Thus, a poly(acrylamide)polymer is said to have a poly(acrylamide) backbone, without regard to the substituents on the acrylamide nitrogen atom, which are components of the polymer side chains. A poly(acrylamide-co-styrene)copolymer, for example, is said to have a mixed acrylamide/styrene backbone.

A "side-chain" refers to a branch off of the polymer backbone. A phosphinyl phosphonate group in a side chain is therefore said be "pendent" from the polymer backbone. The term "spacer group," as used herein, refers to a polyvalent molecular fragment which is a component of a polymer side chain and connects a pendant moiety to the polymer backbone. A spacer group is "inert" when it contains no functionality that substantially interferes with the therapeutic activity of the polymer. Inert spacer groups are preferably hydrocarbyl groups optionally containing one or more linkage groups and are preferably a C1 to C30 alkylene group, more preferably a C1 to C15 group, and even more preferably, a C1 to C8 alkylene group. "Phosphate protecting groups" are groups that are generally removed from both the phosphinyl and phosphonate moieties by hydrolysis, thereby obtaining the free acid or salt form of the phosphinyl phosphonate. Phosphate protecting groups can be chosen so that they are removed at a desired rate or under desired conditions. One example of a phosphate protecting group is an ester of a simple alcohol (e.g., ethanol), diols or polyols (e.g., sugars such as glucose) or polymeric alcohols (e.g., polyvinyl alcohol, polyallyl alcohol, polysaccharides). Phosphate protecting groups also include amines that are capable of forming a phosphorus-nitrogen bond. Another type of phosphate protecting group is an acid halide or other activated carboxylic acid, which can form an acid anhydride with the phosphinyl phosphonate group.

A phosphate protecting group can also be a polymer, which has pendant groups capable of forming a hydrolyzable bond with the phosphinyl phosphonate group. Suitable pendant groups include hydroxyl groups, amine groups and carboxylic acids and derivatives (e.g., acid halides, acid anhydrides, etc.) thereof. Common polymers capable of forming an ester linkage with one of the phosphinyl phosphonate groups contain two or more pendant hydroxyl groups (e.g., polyvinylalcohol), two or more terminal hydroxyl groups (polyethylene glycol, polypropylene glycol), or a combination of at least one pendant hydroxyl group and at least one terminal hydroxyl group (e.g., a polysaccharide, a branched polysaccharide). Phosphinyl phosphonate groups that have a polymer acting as a phosphate protecting group are represented by Structural Formulas (VII)-(XIII), where the polymer protects from one to three of the acidic oxygens:

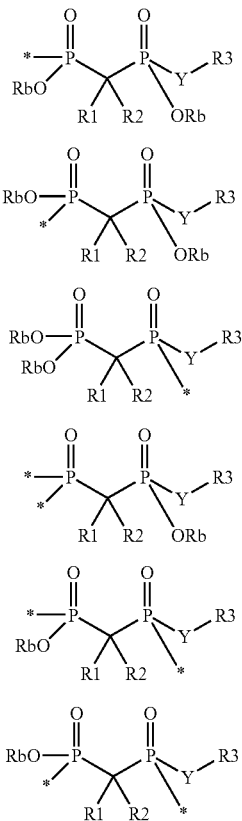

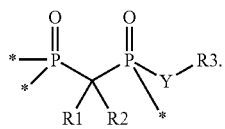

The polymers of the present invention can be homopolymers, which have a uniform backbone composed of a phosphinyl phosphonate functionalized monomers derived from a common polymerizable unit, such as phosphinyl phosphonate functionalized acrylamide. Also included are copolymers and terpolymers, i.e., polymers comprising a mixed backbone of two or three different monomer units, respectively, one or more of which is phosphinyl phosphonate functionalized. Optionally, a copolymer or terpolymer comprises a monomer or repeat unit without a phosphinyl phosphonate group. Examples of such monomer or repeat units are hydrophilic monomer or repeat units, which comprise a hydrophilic group such as an alcohol or carboxamide in the side chain. Examples include:

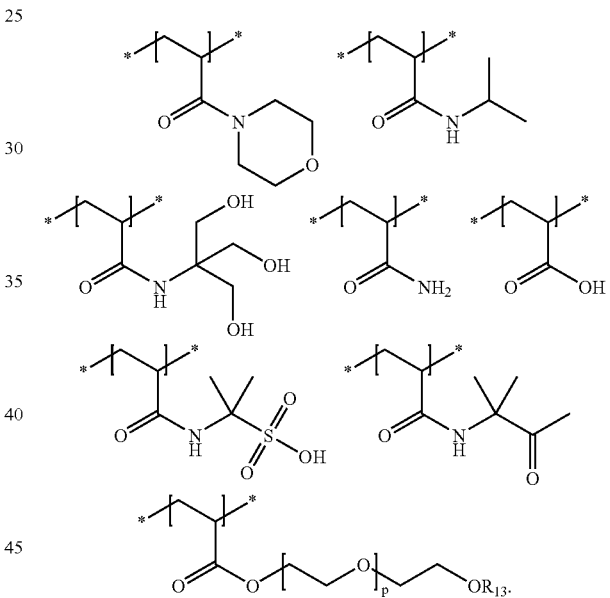

R13 is —H or a lower alkyl group and p is an integer from 1 to 18.

The polymers of the present invention include addition polymers such as a phosphinyl phosphonate functionalized polyacrylate, alkylpolyacrylate, polyacrylamide, alkylpolyacrylamide, poly(allylalcohol), poly(vinylalcohol), poly(vinylamine), poly(allylamine), poly(diallylamine) backbone or a substituted polystyrene backbone. Typically, these addition polymers have side chains comprising phosphinyl phosponate groups. The side chains are typically inert spacer groups such as a straight chained hydrocarbyl group, optionally comprising one or more linking groups, which connect the phosphinyl phosphonate group to the polymer backbone, for example, to carboxylate groups of a polyacrylate, to the amide nitrogens of a polyacrylamide, to the alcohols of a poly(vinylalcohol) or poly(allylalcohol), or to the amines of a poly(vinyl amine,) a poly(allylamine) or a poly(diallylamine) or to a substituent on the phenyl ring of a polystyrene. Polyacrylamide, polymethacrylamide, polyacrylate or polymethacrylate are preferred polymers.

The present invention also includes condensation polymers, which are formed from reactions in which a small molecule such as water is released. Examples include a polyamide, polyalkyleneimine or a polyester. The phosphinyl phosphonate groups can be connected by an inert spacer group to amine or ammonium nitrogens in the backbone of a polyalkyleneimine. For polyamides, the phosphinyl phosphonate groups can be connected to amide nitrogens in the polymer backbone by an inert spacer group. For polyesters, the phosphinyl phosphonate group can be connected by an inert spacer group attached to a carbon atom in the backbone.

Although the molecular weight is not believed to be critical, the upper bound of the molecular weight of polymers of the present invention is typically less than about 500,000 Daltons. The polymers are preferably large enough so that they are not absorbed by the gastrointestinal tract, about 1,000 Daltons. Polymers can weigh from about 1,000 Daltons to about 100,000 Daltons, about 1,000 Daltons to about 50,000 Daltons, about 1,000 Daltons to about 10,000 Daltons or about 2,000 Daltons to about 10,000 Daltons.

Under circumstances when the phosphinyl phosphonate group is sensitive to further reaction, the polymerizable portion of the monomer can be chosen to minimize damage of the phosphinyl phosphonate group. One example is to use a monomer that can be polymerized by the ring opening metathesis polymerization technique, such as the ones shown below:

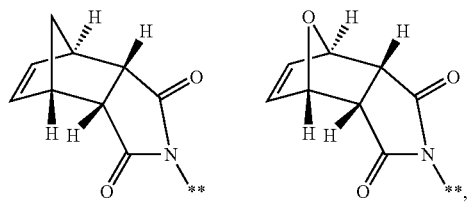

where the inert linking group and the phosphinyl phosphonate are attached via **. Further information about the ROMP technique is located in "Synthesis of Norbomenyl Polymers with Bioactive Oliogpeptides by Ring-Opening Metathesis Polymerization," by H. D. Maynard, et al., *Macromolecules*, 33(17): 6239-6248 (2000) and "Highly Efficient Ring-Opening Metathesis Polymerization (ROMP) Using New Ruthenium Catalysis Containing N-Heterocyclic Carbene Ligands," by C. W. Bielawski, et al., *Angew. Chem. Int. Ed.*, 39(16): 2903-2906 (2000), the contents of which are incorporated herein by reference.

The present invention also includes molecules that contain two phosphinyl phosphonate moieties, referred to herein as "dimers". Such dimers are represented by Structural Formulas (XV), (XVI), (XVII) and (XVIII):

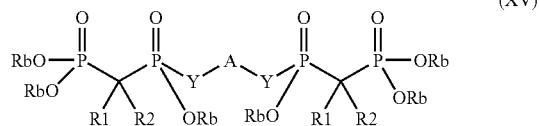 (XV)

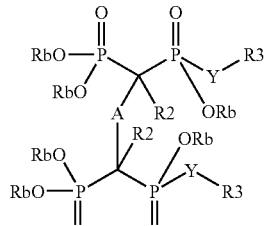 (XVI)

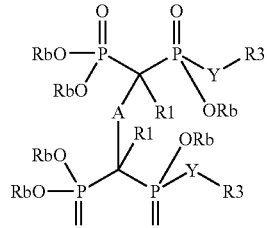 (XVII)

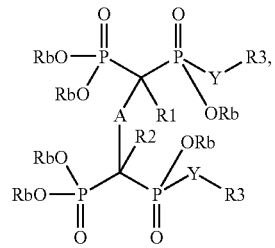 (XVIII)

where the values for R1, R2, R3, A and Y in Structural Formulas (XV)-(XVIII) are as defined above for Structural Formulas (II), (V) and (VI). Preferably, A is an inert linking group, such as a substituted or unsubstituted alkylene group. Y, R1, R2 and R3 are independently chosen, such that the dimers are either symmetrical or asymmetrical. If each corresponding Y, R1, R2 and R3 is the same in both phosphinyl phosphonate groups, the dimer is symmetrical. If any of one the corresponding Y, $R^i$, R2 and R3 variables are not the same between the two phosphinyl phosphonate groups, then the dimer is asymmetrical. Preferably, the dimer is symmetrical.

In the structural formulas depicted herein, the single or double bond by which a chemical group or moiety is connected to the remainder of the molecule or compound is indicated by the following symbol "*".

A "subject" is preferably a human, but can also be an animal in need of treatment with a phosphate transport inhibitor, e.g., companion animals (e.g., dogs, cats, and the like), farm animals (e.g., cows, pigs, horses and the like) and laboratory animals (e.g., rats, mice, guinea pigs and the like).

Subjects "in need of phosphate transport inhibition" include subjects with diseases and/or conditions that can be treated with phosphate transport inhibitors to achieve a beneficial therapeutic and/or prophylactic result. A beneficial outcome includes a decrease in the severity of symptoms or delay in the onset of symptoms, increased longevity and/or more rapid or more complete resolution of the disease or condition. For example, a subject in need of treatment typically has elevated serum phosphate levels, hyperphosphatemia resulting from, for example, impaired kidney function, or hypoparathyroidism. Lower serum phosphate levels can be achieved, for example, by inhibiting phosphate transport in the intestines. A subject "in need of treatment" also includes a subject with chronic renal failure who may have serum phosphate levels within the normal range. Inhibition of phosphate transport in the intestine or kidneys can slow rate of renal deterioration in these subjects, and decrease the risk of cardiovascular events. Other examples of subjects in need of phosphate transport inhibitors include patients with a disease associated with disorders of phosphate metabolism or a disease medicated by impaired phosphate transport function. Examples of diseases and/or disorders of this type include soft tissue calcification, such as cardiovascular calcification, hyperparathyroidism, uremic bone disease, renal bone disease and osteoporosis.

An "effective amount" of a small molecule or polymer disclosed herein is a quantity that results in a beneficial clinical outcome of the condition being treated with the compound or polymer compared with the absence of treatment. The amount of compound or polymer administered will depend on the degree, severity, and type of the disease or condition, the amount of therapy desired, and the release characteristics of the pharmaceutical formulation. It will also depend on the subject's health, size, weight, age, sex and tolerance to drugs. Typically, the compound or polymer is administered for a sufficient period of time to achieve the desired therapeutic effect. Typically between about 5 g per day and about 0.001 g per day of the compound or polymer (preferably between about 1 g per day and about 0.001 g per day) is administered to the subject in need of treatment.

The compounds and polymers can be administered by any suitable route. The compound or polymer is preferably administrated orally (e.g., dietary) in capsules, suspensions or tablets. Methods for encapsulating compositions (such as in a coating of hard gelatin or cyclodextran) are known in the art (Baker, et al., "Controlled Release of Biological Active Agents", John Wiley and Sons, 1986). The compound or polymer can be administered to the subject in conjunction with an acceptable pharmaceutical carrier as part of a pharmaceutical composition. The formulation of the pharmaceutical composition will vary according to the route of administration selected. Suitable pharmaceutical carriers may contain inert ingredients which do not interact with the compound. The carriers should be biocompatible, i.e., non-toxic, non-inflammatory, non-immunogenic and devoid of other undesired reactions at the administration site. Examples of pharmaceutically acceptable carriers include, for example, saline, commercially available inert gels, or liquids supplemented with albumin, methyl cellulose or a collagen matrix. Standard pharmaceutical formulation techniques can be employed, such as those described in Remington's Pharmaceutical Sciences, Mack Publishing Company, Easton, Pa.

For oral administration, the compounds and polymers can be formulated readily by combining the active compounds with pharmaceutically acceptable carriers well known in the art. Such carriers enable the compounds and polymers of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound or polymer doses.

Pharmaceutical preparations that can be used orally include push-fit capsules made of a suitable material, such as gelatin, as well as soft, sealed capsules made of a suitable material, for example, gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

Compounds and polymers of the present invention can be administered as prodrugs and formulated as described above. A prodrug is converted into the active drug substance in vivo, after administration to a subject. Typically, the acidic oxygens of an unsaturated phosphinyl phosphonate are blocked in the prodrug form, such as by an alkyl ester, and these blocking groups are released (e.g., by hydrolysis) in vivo. The blocking group can either be a small molecule or a polymer. The number and/or type of blocking groups can be varied in order to control the duration of the blocking effect and/or the conditions under which the blocking group is released.

It will be understood that, certain compounds of the invention may be obtained as different stereoisomers (e.g., diastereomers and enantiomers) and that the invention includes all isomeric forms and racemic mixtures of the disclosed compounds and a methods of treating a subject with both pure isomers and mixtures thereof, including racemic mixtures. Stereoisomers can be separated and isolated using any suitable method, such as chromatography.

The activity of compounds of the present invention can be assessed using suitable assays, such as the $^{33}PO_4$ Uptake In Rabbit Intestinal BBMV High Throughput Screening (HTS) assay, as described in the Example 28. Compounds of the present invention can also be identified by virtue of their ability to inhibit the absorption of phosphate in vivo, for example, in the gastrointestinal tract of a laboratory animal.

The compounds disclosed herein can be prepared accordingly as shown in Examples 1-27. The schemes are described in greater detail below.

The phosphate transport inhibitors of the present invention can be administered as a monotherapy (e.g., as the sole active ingredient) or as a combination therapy. Examples of combination therapies are discussed below.

In certain instances it may be advantageous to co-administer one or more additional pharmacologically active agents along with a compound or polymer of the present invention. Examples include pharmaceutically active calcium, aluminum or lanthanum-containing phosphate binders or pharmaceutically active phosphate-binding polymers such as those disclosed in U.S. Pat. Nos. 5,496,545, 5,667,775 and 6,083, 495; the contents of which are incorporated herein by reference in their entirety. Preferably the pharmacologically active agent is a polyallylamine phosphate-binding polymer. More preferably, the pharmacologically active agent is an epichlorohydrin-cross-linked poly(allylamine hydrochloride) resin, also referred to as sevelamer hydrochloride or sevelamer and marketed as RENAGEL® (Gel Tex Pharmaceuticals, Inc., Waltham, Mass.).

It may be advantageous to co-administer a compound or polymer of the invention with one or more pharmaceutically acceptable metal ion sequestrants, such as a calcium sequestrant. Examples of calcium sequestrants include small molecules such as ethylenediamine triacetic acid (EDTA), citrates and citric acid, carbonates, silicates. Calcium sequestrants can also be polymers with acid functional groups, including polyacrylates, lignosulfonates, poly(aspartic acid), polysuccinimide and polystyrene sulfonates.

The invention is illustrated by the following examples, which are not intended to be limiting in any way.

EXEMPLIFICATION

Example 1

(n-decyl)phosphono chloridic acid, ethyl ester

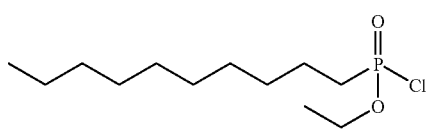

To a 500 mL round bottomed flask containing n-decylphosphonic acid diethyl ester, 22 g (79.0 mmol) was added to 100 mL of diethylether. This solution was stirred and cooled to −20° C. using an ice/salt water bath. Oxalyl Chloride (20.06 g, 158 mmol) was added in small portions over 45 minutes while maintaining the temperature at −20° C. The reaction mixture was then allowed to warm to room temperature and stirred for 24 hours. The solvent was removed by rotary evaporation to give a viscous liquid. The liquid was purified by vacuum distillation (boiling point: 126° C. at 0.4 mmHg) to give 15.5 g (73% yield) of the desired product. $^1$H NMR (400 MHz CDCl$_3$): δ 4.2 (m, 2H), 2.0 (m, 2H), 1.6 (m, 2H), 1.2 (m, 17H), 0.75 (t, 3H).

Example 2

((n-decyl)ethoxyphosphinyl)methylphosphonic acid dimethyl ester

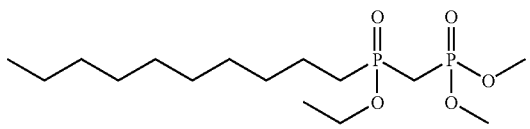

A 2.5 M hexane solution of n-butyl lithium (25.5 mL, 63.75 mmol) was added dropwise with stirring to methylphosphonic acid dimethyl ester (7.38 g, 59.55 mmol) in 130 mL of anhydrous tetrahydrofuran at −78° C. under nitrogen atmosphere. After the addition was complete (20 minutes) the reaction was stirred for 30 minutes. Then (n-decyl) phosphono chloridic acid, ethyl ester (8 g, 29.77 mmol) was added slowly while maintaining the reaction temperature at −78° C. After the addition was complete the reaction mixture was stirred for 60 minutes at −78° C. and then allowed to warm to −50° C. where the excess base was neutralized by the addition of saturated ammonium chloride. The reaction was allowed to warm to ambient temperature and stirred for a period of 16-20 hours. The volatiles were removed by rotary evaporation to give a viscous liquid. This liquid was diluted with water (75 mL) and extracted twice with dichloromethane (120 mL). The organic layer was dried over magnesium sulfate, then filtered and concentrated under rotary evaporation to give 13 g of a viscous liquid. The liquid was then distilled under vacuum (boiling point 167° C. at 0.05 mmHg) to give ((n-decyl)ethoxyphosphinyl)methylphosphonic acid dimethyl ester (5.43 g, 52% yield).
$^1$H NMR (400 MHz CDCl$_3$): δ 3.8 (m, 2H), 3.5 (m, 6H), 2.1 (m, 2H), 1.6 (m, 2H), 1.3 (m, 2H), 1.0 (m, 17H), 0.5 (t, 3H).

Example 3

((n-decyl)hydroxyphosphinyl)methylphosphonic acid trisodium salt

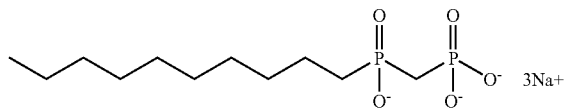

Bromotrimethylsilane (2 mL, 15.15 mmol) was added dropwise to ((n-decyl)ethoxyphosphinyl)methylphosphonic acid dimethyl ester (0.6 g, 1.68 mmol) in a 30 vial. A large exotherm was noted which resulted in a clear solution that was stirred for 14-16 hours at ambient temperature. Excess bromotrimethylsilane was then removed by passing a steady stream of nitrogen over the solution for 2 hours. The solution was then placed under high vacuum for 3 hours to remove any residual bromotrimethylsilane. A tacky solid was obtained. Tributylamine (0.936 g, 5.05 mmol), methanol (10 mL) and deionized water (0.5 mL) was then added to the vial and a clear solution was obtained. This solution was then added dropwise to a 0.5 M solution of NaI in acetone (10.1 mL, 5.05 mmol). A white solid precipitated immediately which was then washed with 20 mL of acetone. The solid was filtered under vacuum and then washed several times with acetone. The white solid recovered was placed under vacuum to dry for a period of 12-16 hours to give the desired product (0.481 g, 78% yield). $^1$H NMR (400 MHz D$_2$O): δ 1.6 (m, 2H), 1.4 (m, 2H), 1.2 (m, 2H), 1.0 (m, 14H), 0.5 (t, 3H).

Example 4

(n-heptadecyl)-2-propoxyphosphinyl)methylphosphonic acid di-2-propoxy ester

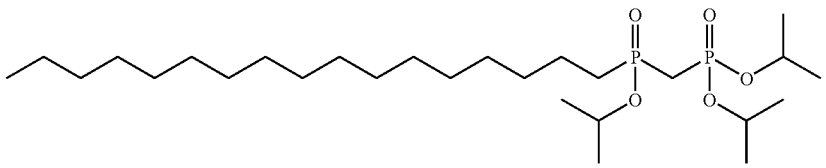

Sodium hydride (95%, 0.093 g, 3.875 mmol) and anhydrous tetrahydrofuran (12 mL) was added to a 30 mL vial under a nitrogen atmosphere. This mixture was stirred magnetically while (methyl-2-propoxyphosphinyl)methylphosphonic acid di-2-propoxy ester (1 g, 3.33 mmol) was added dropwise. Hydrogen gas was given off. The reaction mixture was stirred for 1 hour at ambient temperature and then cooled to −78° C. using a dry ice acetone bath. A 2.5 M solution of n-butyl lithium in hexane (1.5 mL, 3.75 mmol) was added dropwise keeping the reaction temperature below −70° C. The reaction was stirred for 15 minutes after which 1-iodohexadecane (1.24 g, 3.52 mmol) was added dropwise. Again the reaction temperature was maintained below −70° C. After the addition was complete, the solution became cloudy and was stirred for 2 hours. The reaction mixture was then allowed to warm to ambient temperature. The excess base was neutralized by the addition of benzoic acid (1 g) dissolved in tetrahydrofuran (4 mL). The tetrahydrofuran was removed by rotary evaporation to give a pale creamy solid. The solid was dissolved in water (140 mL) and extracted with dichloromethane (200 mL). The organic layer was extracted with saturated NaHCO$_3$ (140 mL) and then extracted with saturated NaCl solution (140 mL). The dichloromethane solution was dried over sodium sulfate and then concentrated under rotary evaporation to give a viscous liquid. The liquid was then purified by flash chromatography (silica mesh size 230-400) eluted with ethyl acetate/EtOH (95:5) to give the desired product (0.32 g, 85% yield).

Example 5

((n-heptadecyl)-hydroxyphosphinyl)methylphosphonic acid tri-sodium salt

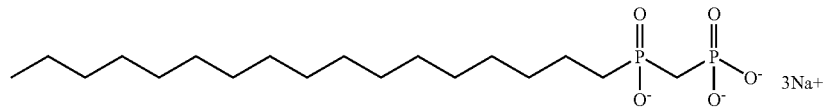

Bromotrimethylsilane (0.34 mL, 2.58 mmol) was added dropwise to ((n-heptadecyl)-2-propoxyphosphinyl)methylphosphonic acid di-2-propoxy ester (0.150 g, 0.286 mmol) in a 3 mL vial. The resulting solution was stirred for 14-16 hours at ambient temperature. Excess bromotrimethylsilane was then removed by passing a steady stream of dry nitrogen over the solution for 2 hours. The solution was then placed under high vacuum for 3 hours to remove any residual bromotrimethylsilane. Tributylamine (0.24 g, 1.29 mmol) and methanol (2 mL) were then added to the vial resulting in a clear solution. This solution was then added dropwise to a 0.5 M solution of NaI in acetone (5.0 mL, 2.5 mmol). A white precipitated immediately appeared. The solid was collected by centrifugation and the acetone solution was discarded. The solid was then washed by suspension in clean acetone (20 mL), centrifugation and removal of acetone supernatant. After this washing procedure was completed 3 times, the solid was placed under vacuum for a period of 12-16 hours providing the desired product (0.113 g, 85% yield). $^1$H NMR (400 MHz D$_2$O): δ 1.7 (m, 2H), 1.3 (m, 4H), 1.1 (m, 28H), 0.7 (t, 3H).

Example 6

11-undecenyl phosphonic acid diethyl ester

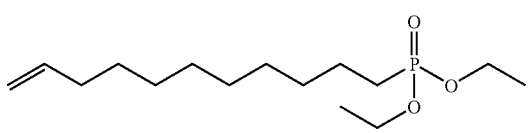

Sodium iodide (27 g, 18 mmol, 1.6 eq.) was added to a solution of 1-bromo-1-undecene (27 g, 11.6 mmol) in acetone (250 mL) and the mixture was stirred overnight. The mixture was then diluted with water (100 mL) and the organic solvent removed. The mixture was extracted with ethyl acetate (250 mL). The organic layer was dried over Na$_2$CO$_3$, filtered and the solvent removed to dryness revealing 1-iodo-10-undecene, which was used without further purification. $^1$H NMR (400 MHz CDCl$_3$) δ=5.8 (m, 1H), 4.9 (m, 2H), 3.2 (t, 2H), 2.05 (sq, 2H), 1.7 (sq, 2H), 1.4-1.2 (m, 12H). A mixture of 1-iodo-10-undecene (15.2 g, 53.7 mmol), and triethyl phosphite (60 mL, 350 mmol, 6.5 eq.) was heated to 130° C. for 20 hours. The diethyl ethyl phosphonate was removed by vacuum distillation. The product was used without further purification. $^1$H NMR (400 MHz CDCl$_3$) δ=5.8 (m, 1H), 4.9 (m, 2H), 4.0 (m, 4H), 2.0 (sq, 2H), 1.7 (m, 2H), 1.5 (m, 2H), 1.4-1.2 (m, 18H). $^{31}$P NMR(CDCl$_3$) δ=33.7.

Example 7

(10-undecenyl)phosphono chloridic acid, ethyl ester

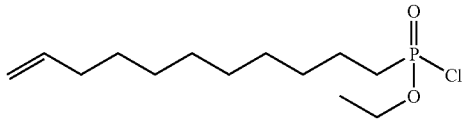

A solution of 10-undecenylphosphonic acid diethyl ester (53.51 g, 180 mmol) in CH$_2$Cl$_2$ (350 mL) was cooled to about −8° C. Oxalyl chloride (32 mL, 370 mmol, 2 eq.) was added slowly to the mixture, the mixture was warmed to room temperature and stirred overnight. Solvent was removed to dryness and the excess oxalyl chloride was azeotropically removed with hexane three times (100 mL). The mixture was dried in a vacuum oven at 40° C. overnight and the product was used without further purification.

$^1$H NMR (400 MHz CDCl$_3$) δ=5.8 (m, 1H), 5.0 (m, 2H), 4.3 (m, 2H), 2.2-2.0(m, 4H), 1.7 (m, 2H), 1.5-1.2 (M, 15H). $^{31}$P NMR (CDCl$_3$) δ=46.2.

Example 8

((10-undecenyl)-ethoxyphosphinyl)methylphosphonic acid dimethyl ester

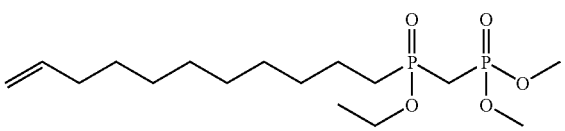

A 2.5 M solution of n-butyllithium in hexane (9.4 mL, 23.5 mmol) was added dropwise with stirring to methylphosphonic acid dimethyl ester (2.65 g, 21.4 mmol) in 100 mL of anhydrous tetrahydrofuran at −78° C. under a nitrogen atmosphere. After 30 minutes, (10-undecenyl)phosphono chloridic acid, ethyl ester (3 g, 10.68 mmol) was added dropwise while stirring was continued. The reaction was stirred at −78° C. for 2 hours then warmed to −50° C. and stirred for an additional 2 hours. Saturated ammonium chloride was then added to neutralize the excess base and the reaction was allowed to warm to ambient temperature. The volatiles were removed by rotary evaporation to give a viscous liquid. This liquid was diluted with ethyl acetate (200 mL) and extracted twice with water (100 mL). The organic layer was collected and dried over sodium sulfate, filtered and concentrated under rotary evaporation to give a viscous liquid. The product was then placed on a high vacuum pump to remove any remaining volatiles (3.07 g, 78% yield).

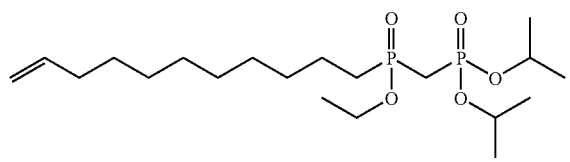

Example 9

((10-undecenyl)-ethoxyphosphinyl)methylphosphonic acid diisopropyl ester

The procedure described above in the preparation of ((10-undecenyl)-ethoxyphosphinyl)methylphosphonic acid dimethyl ester (Example 8), was used to obtain the diisopropyl ester by substituting methylphosphonic acid diisopropyl ester in place of methylphosphonic acid dimethyl ester.

Example 10

((10-undecenyl)-hydroxyphosphinyl)methylphosphonic acid tri sodium salt

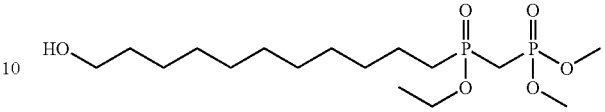

Bromotrimethylsilane (0.8 mL, 6.06 mmol) was added dropwise to ((10-undecenyl)-ethoxyphosphinyl)methylphosphonic acid dimethyl ester (0.250 g, 0.68 mmol) in a 3 mL vial. This solution was stirred for 14-16 hours at ambient temperature. Excess bromotrimethylsilane was removed by passing a steady stream of dry nitrogen over the solution for 2 hours. The residue was then placed under high vacuum for 3 hours to remove residual bromotrimethylsilane. Tributylamine (0.57 g, 3.08 mmol) and methanol (3 mL) was then added to the residue resulting in a clear solution. This mixture was added dropwise to a 0.5 M solution of NaI in acetone (10 mL, 5.0 mmol). A white solid precipitated immediately. The solid was collected by centrifugation and the acetone solution was discarded. The solid was then washed by suspension in clean acetone (20 mL), centrifugation and removal of acetone supernatant. After this washing procedure was completed 3 times, the solid was placed under vacuum for a period of 12-16 hours providing the desired product (0.19 g, 74% yield).

$^1$H NMR (400 MHz D$_2$O): δ 5.8 (m, 1H), 4.9 (m, 2H), 1.9 (m, 4H), 1.6 (m, 2H) 1.2 (m, 14H).

Example 11

((11-hydroxyundecyl)-ethoxyphosphinyl)methylphosphonic acid dimethyl ester

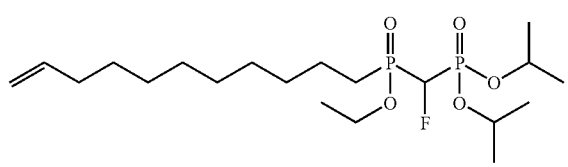

A 1.0 M tetrahydrofuran solution of borane (81.5 mL, 81.5 mmol) was added to a flask containing anhydrous tetrahydrofuran (450 mL) under a nitrogen atmosphere. The solution was cooled to −10° C. using an ice/salt water bath. ((10-undecenyl)-ethoxyphosphinyl)methylphosphonic acid dimethyl ester (30 g, 81.4 mmol) was added slowly to the borane solution. The reaction mixture was stirred at −10° C. for 15 minutes and then warmed to ambient temperature and stirred for 2 hours. The solution was again cooled to −10° C. and 1N NaOH (81.4 mL, 81.4 mmol) was added dropwise in a manner that controlled the frothing. This addition was followed by the addition of a 30 wt % hydrogen peroxide solution (28.6 g). This mixture was then heated to 50° C. for 2 hours and then allowed to cool to ambient temperature. The excess peroxide was then reduced by the addition of aqueous sodium bisulfite (22 g in 120 mL water). The volatiles were removed by rotary evaporation to give a viscous liquid. The liquid was dissolved in ethyl acetate (800 mL) and then extracted twice with water (500 mL). The water layer was collected and extracted with ethyl acetate (600 mL). The organic extracts were combined and dried over sodium sulfate. The solvent was then removed by rotary evaporation revealing a viscous liquid. The liquid was placed under high vacuum to remove remaining volatiles providing the desired product (28.5 g, 90% yield). $^1$H NMR (400 MHz CDCl$_3$): δ 4.0 (m, 2H), 3.7 (m, 6H), 3.5 (t, 2H), 2.3 (m, 2H), 1.8 (m, 2H), 1.5 (m, 4H), 1.2 (m, 18H).

Example 12

Fluoro((10-undecenyl)-ethoxyphosphinyl)methylphosphonic acid diisopropyl ester

A 1 M solution of sodium bistrimethylsilylamide in tetrahydrofuran (30 mL, 30 mmol) was added dropwise with stirring to ((10-undecenyl)-ethoxyphosphinyl)methylphosphonic acid diisopropyl ester (11 g, 25.9 mmol) in anhydrous tetrahydrofuran (100 mL) at −78° C. under a nitrogen atmosphere. After the addition was complete (15 minutes) the solution was stirred for 45 minutes after which n-fluorobenzenesulfonimide (10 g, 31.7 mmol) in anhydrous tetrahydrofuran (30 mL) was added. The reaction was stirred for 3 hours at −78° C. The reaction was then warmed to −50° C., and excess base was neutralized by the addition of saturated ammonium chloride. The mixture was warmed to room temperature and the volatiles were removed by rotary evaporation to give a creamy solid. The solid was dissolved in water (300 mL) and then extracted three times with ethyl acetate (350 mL). The organic layers were combined and extracted with saturated sodium bicarbonate (250 mL). The ethyl acetate layer was dried over sodium sulfate and volatiles were removed by rotary evaporation to give a viscous liquid. The liquid was purified by flash chromatography (500 g silica, ethyl acetate/ethanol=9.5/0.5) to give the desired product (3.1 g, 27% yield).

Example 13

Fluoro((10-undecenyl)-hydroxyphosphinyl)methylphosphonic acid trisodium salt

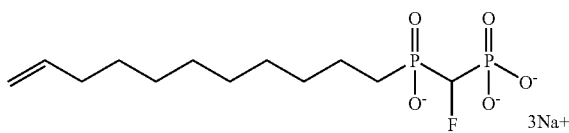

Bromotrimethylsilane (4.0 mL, 30.31 mmol) was added dropwise to fluoro((10-undecenyl)-ethoxyphosphinyl)methylphosphonic acid diisopropyl ester (1.5 g, 0.68 mmol) in a 40 mL vial. The solution was stirred for 14-16 hours at ambient temperature. Excess bromotrimethylsilane was then removed by passing a steady stream of nitrogen over the solution for 2 hours. The solution was then placed under high vacuum for 3 hours to remove any residual bromotrimethylsilane. A sticky residue was revealed. Tributylamine (2.83 g, 15.26 mmol) and methanol (5 mL) was then added to give a clear solution. This solution was then added dropwise to a solution of 0.5 M NaI in acetone (50 mL, 25.0 mmol). A white solid precipitated immediately. The solid was collected by centrifugation and the acetone solution was discarded. The solid was then washed by suspension in clean acetone (25 mL), centrifugation and removal of acetone supernatant. After this washing procedure was completed 3 times, the solid was placed under vacuum for a period of 12-16 hours providing the desired product (1.05 g, 74% yield). $^1$H NMR (400 MHz D$_2$O): δ 5.8 (m, 1H), 4.9 (m, 2H), 4.4 (m, 1H), 1.9 (m, 2H) 1.6 (m, 2H), 1.4 (m, 2H), 1.2 (m, 12H).

Example 14

((11-N-phthalimidoundecyl)-ethoxyphosphinyl)methylphosphonic acid dimethyl ester

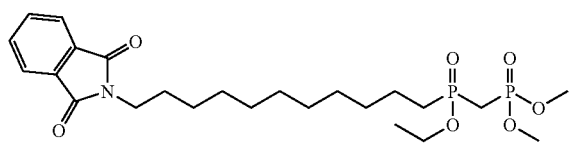

((11-hydroxyundecyl)-ethoxyphosphinyl)methylphosphonic acid dimethyl ester (32.41 g, 83.96 mmol) was dissolved in anhydrous tetrahydrofuran (600 mL). Triphenyl phosphine (46.95 g, 179 mmol. 2.1 eq.) and phthalamide (26.09 g, 177 mmol, 2.1 eq.) was added to the mixture. The mixture was cooled to about 0° C., and diethyl azodicarboxylate (28.0 mL, 1.78 mmol, 2.1 eq.) was added slowly, keeping the temperature below 22° C. The mixture was stirred at room temperature overnight. The solvent was then removed and diethyl ether (1 L) was added to the mixture. The mixture was stirred for at least 1 hour and then filtered. The solvent was removed to dryness and more diethyl ether (600 mL) was added. The mixture was stirred for at least an hour and filtered. The solvent was removed to dryness revealing the crude product. The crude product was purified by column chromatography (silica, ethyl acetate/methanol=10/0.5) to obtain the desired product (37.15 g, 86% yield). $^1$H NMR (CDCl$_3$) δ=7.85 (s, 2H), 7.65 (s, 2H), 4.2 (m, 2H), 3.8 (d, 6H), 3.85 (t, 2H), 2.4 (m, 2H), 1.9 (m, 2H), 1.6 (m, 2H), 1.4-1.2 (m, 17H). $^{31}$P NMR (CDCl$_3$) δ=48, 24.

Example 15

((11-N-phthalimidoundecyl)-hydroxyphosphinyl)methylphosphonic acid trisodium salt

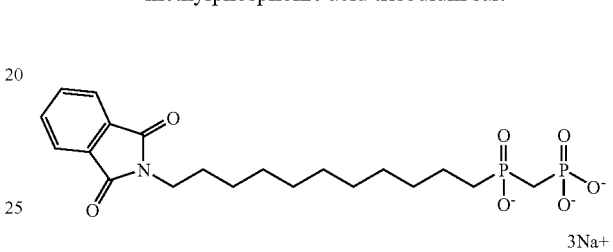

((11-N-phthalimidoundecyl)-ethoxyphosphinyl)methylphosphonic acid dimethyl ester (0.176 g, 0.34 mmol) was dissolved in CH$_2$Cl$_2$ (1.5 mL) and bromotrimethylsilane (0.3 mL, 2.3 mmol, 6.7 eq.) was added to the mixture under a dry nitrogen atmosphere. The mixture was stirred overnight. The next day the volatiles were removed to dryness. Excess bromotrimethylsilane was azeotropically removed with methanol three times (10 mL). The resulting residue was dissolved in methanol (7 mL) and filtered through a PTFE 0.2 μM membrane. n-Butyl amine (0.35 mL) was then added to the methanol filtrate. This solution was then added dropwise to a solution of NaI (0.22 g) in acetone. A white solid precipitated immediately. The solid was collected by centrifugation and the acetone solution was discarded. The solid was then washed by suspension in clean acetone (25 mL), centrifugation and removal of acetone supernatant. After this washing procedure was completed 5 times, the solid was dried in vacuum oven at 40° C. overnight. $^1$H NMR (D$_2$O) δ=7.6 (br, 4H), 3.4 (t, 2H), 1.8 (m, 2H), 1.4 (m, 4H), 1.2 (m, 2H), 1.2-1.0 (m, 14H). $^{31}$P NMR (d$_4$-methanol) δ=18, 48. M/Z of (M-H)$^-$=458.

Example 16

((11-aminoundecyl)-hydroxyphosphinyl)methylphosphonic acid

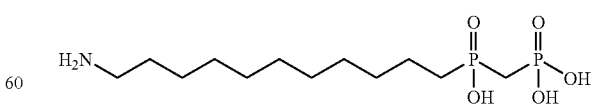

((11—N-phthalimidoundecyl)-ethoxyphosphinyl)methylphosphonic acid dimethyl ester (37.15 g, 78 mmol) was dissolved in a mixture of 2-propanol (165 mL) and water (26 mL). The mixture was cooled to about 10° C. in an ice bath and NaBH$_4$ (11.11 g, 293 mmol, 3.8 eq.) was added slowly.

The mixture was filtered and then cooled to below 5° C. in an ice bath. Acetic acid (70 mL) was then added slowly to the mixture. When the addition was complete the mixture was heated to 90° C. for 6 days. The mixture was then cooled to room temperature and the solvent removed. Residual water and acetic acid were removed from the residue azeotropically using ethyl acetate (200 mL), and then again using acetone two times (500 mL) and then again using toluene two times (500 mL). The resulting residue was free from acetic acid. This residue was partitioned between water (300 mL) and ethyl acetate (300 mL). The layers were separated and the organic layer was discarded. The aqueous layer was lyophilized to give a mixture of inorganic salts and ((11-aminoundecyl)-ethoxyphosphinyl)methylphosphonic acid. This solid was suspended in HCl (36%, 75 mL) and heated to 90° C. overnight. A clear solution was obtained. The mixture was cooled to room temperature and a solid precipitate formed. This solid was removed by centrifugation and found (by NMR) to contain no product. This solid was discarded. The supernatant was concentrated and again a solid appeared as a suspension in solution. HCl was removed from this suspension azeotropically using water (100 mL). After removal of HCl, an oily suspension was obtained. When additional water was added (100 mL), the product appeared as a white solid. This solid was collected by centrifugation. The solid was washed two times with acetone (70 mL) and dried in vacuum oven at 35° C. (recovery=9.98 g). A second crop was obtained by concentrating the supernatant and heating it with HCl (36%, 40 mL) for 2 hours. The solvent was removed to dryness and the mixture was suspended in water (20 mL), centrifuged to collect solid product, and the solid was washed with water (10 mL) and two times with acetone (20 mL) (recovery=2 g). $^1$H NMR (D$_2$O) δ=2.3 (t, 2H), 1.6 (t, 2H), 1.4 (m, 2H), 1.2-1.0 (m, 18H). $^{31}$P NMR (D$_2$O) δ=13.8, 42.6.

Example 17

(4-pentenyl)phosphonic acid diethyl ester

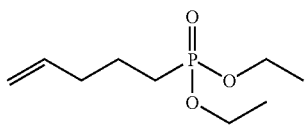

Sodium iodide (100.6 g, 0.66 mol, 1.1 eq.) was added to a solution of 1-bromo-4-pentene (100 g, 0.67 mol) in acetone (250 mL) and the mixture was stirred at room temperature overnight. The mixture was filtered and the solid was washed with acetone. The acetone filtrate and the acetone wash were combined. The acetone was then removed by distillation, revealing 1-iodo-4-pentene, which was used in the next step.

$^1$H NMR (CDCl$_3$) δ=5.8 (m, 1H), 5.0 (m, 2H), 3.2 (t, 2H), 2.2 (sq, 2H), 1.8 (sq, 2H). Triethyl phosphite (400 mL, 2.3 mol, 3.5 eq.) was added to the 1-iodo-4-pentene, and the mixture was heated to 130° C. for three hours. Diethyl ethyl phosphonate was removed by fractional vacuum distillation, revealing the desired 4-pentenyl phosphonic acid diethyl ester which was used without further purification. $^1$H NMR (CDCl$_3$) δ=5.7 (m, 1H), 4.8 (m, 2H), 4.0 (m, 4H), 2.0 (sq, 2H), 1.7 (m, 4H), 1.2 (t, 6H). $^{31}$P NMR (CDCl$_3$) δ=33.3.

Example 18

1-pentadecene-5-phosphonic acid diethyl ester

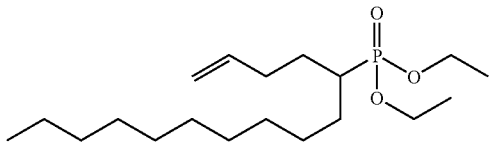

A solution of 4-pentenyl phosphonic acid diethyl ester (2.832 g, 13.7 mmol) in anhydrous tetrahydrofuran (20 mL) and cooled to about −78° C. A 1.3 M solution of sec-butyl lithium in cyclohexane (15 mL, 19.5 mmol) was added slowly to the mixture keeping the temperature below −60° C. 1-Iododecane (6.32 g, 23.6 mmol, 1.8 eq.) was then added slowly to the reaction mixture. The mixture was warmed to 0° C. and was stirred for three hours. The reaction was then quenched with NH$_4$Cl (saturated, 20 mL). The mixture was warmed to room temperature and the THF was removed by rotary evaporation. The resulting solution was extracted with ethyl acetate (50 mL). The organic layer was separated and dried over Na$_2$CO$_3$. The solvent was removed and the resulting residue was purified by column chromatography (silica, ethyl acetate/hexane=2/8 then 4/6) to provide the pure product (3.46 g, 73% yield). $^1$H NMR (CDCl$_3$) δ=5.8 (m, 1H), 5.0 (m, 2H), 4.1 (m, 4H), 2.2 (m, 2H), 1.8-1.2 (m, 27H), 0.9 (t, 3 H). $^{31}$P NMR (CDCl$_3$) δ=35.8.

Example 19

(1-pentadecenyl)-5-phosphono chloridic acid ethyl ester

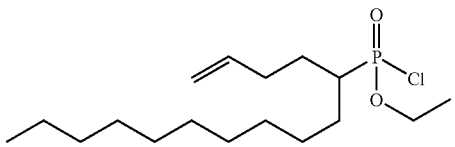

A solution of 1-pentadecene-5-phosphonic acid diethyl ester (3.46 g, 10 mmol) in CH$_2$Cl$_2$ (5 mL) was cooled in an ice bath. Oxalyl chloride (1.85 mL, 21.2 mmol, 2 eq.) was added slowly to the solution. When the addition was complete, the reaction was warmed to room temperature and stirred overnight. A second portion of oxalyl chloride (1.85 mL, 21.2 mmol, 2 eq.) was then added, and the reaction was stirred overnight. The solvent was removed to dryness and excess oxalyl chloride was azeotropically removed with hexane three times (100 mL). The mixture was dried in vacuum oven at 40° C. overnight. The crude product was used without further purification. $^{31}$P NMR (CDCl$_3$) δ=51.2.

Example 20

(1-pentadecenyl-5-ethoxyphosphinyl)methylphosphonic acid dimethyl ester

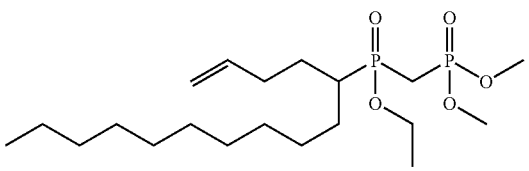

This material was prepared from (1-pentadecenyl)-5-phosphono chloridic acid ethyl ester using the methodology as described for the preparation of ((10-undecenyl)-ethoxyphosphinyl)methylphosphonic acid dimethyl ester. The product was purified by column chromatography (silica, ethyl acetate then ethyl acetate/methanol=10/0.5). $^1$H NMR (CDCl$_3$) δ=5.8 (m, 1H), 5.0 (m, 2H), 4.2 (m, 4H), 3.8 (d, 6H), 2.4 (m, 2H), 2.2 (m, 2H), 2.0-1.3 (m, 27H), 0.9 (t, 3H). $^{31}$P NMR (CDCl$_3$) δ=51, 24.5.

Example 21

(1-pentadecenyl-5-hydroxyphosphinyl)methylphosphonic acid trisodium salt

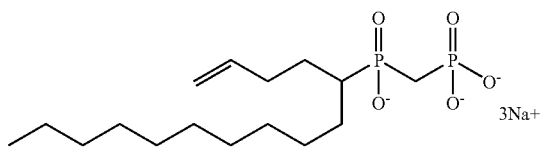

This material was prepared from the triester using the methodology as described for the preparation of sodium ((11-N-phthalimidoundecyl)-hydroxyphosphinyl)methylphosphonic acid trisodium salt. M/Z of (M-H)$^-$=367.

Example 22

(1-(10-undecenyl-ethoxyphosphinyl))hexylphosphonic acid diethyl ester

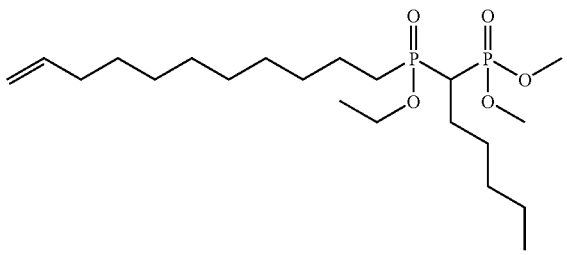

((10-undecenyl)-ethoxyphosphinyl))methylphosphonic acid dimethyl ester (0.83 g, 2.25 mol) was dissolved in anhydrous dimethylformamide (3 mL) and placed in an ice bath. Sodium hydride (60 mg, 2.5 mmol, 1.1 eq.) was added slowly. The mixture was warmed to room temperature and 1-iodopentane (0.35 mL, 2.68 mmol, 1.2 eq.) was added. The reaction was stirred overnight. The next day, a solution of NH$_4$Cl (saturated, 8 mL) was added to the reaction mixture. The reaction was then extracted with ethyl acetate. The organic layer was separated, dried over Na$_2$CO$_3$ and filtered. The solvent removed by rotary evaporation. The residue was purified by column chromatography (silica, ethyl acetate/hexane/methanol 5/5/0.5) to obtain pure product (0.158 g). $^1$H NMR (CDCl$_3$) δ=5.8 (m, 1H), 5.0 (m, 2H), 4.2 (m, 4H), 3.6 (d, 6H), 2.2 (dt, 1H), 2.0-1.3 (m, 27H), 0.9 (t, 3H). $^{31}$P NMR (CDCl$_3$) δ=53, 53.7, 28.5.

Example 23

(1-(10-undecylhydroxyphosphinyl))hexylphosphonic acid trisodium salt

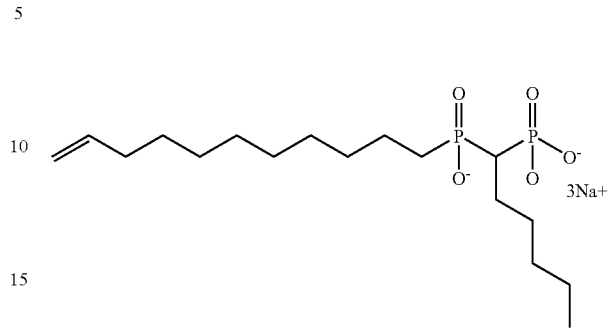

This material was prepared from the triester using the methodology as described for the prepararion of (1-(undecenylethoxyphosphinyl))phosphonic acid trisodium salt. M/Z of (M-H)$^-$=381.

Example 24

General procedure for the preparation of sulfonamide/amide derivatives ((11-aminoundecyl)-hydroxyphosphinyl)methylphosphonic acid

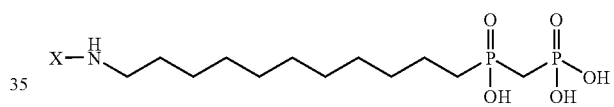

((11-aminoundecyl)-hydroxyphosphinyl)methylphosphonic acid (0.15 mmol) was suspended in a mixture of water (0.5 mL)/tetrahydrofuran (1 mL), and a solution of NaOH (1.2 M, 0.2 mL, 2.4 mmol, 16 eq.) was added. The mixture was placed in an ice bath and the desired sulfonyl chloride or acid chloride (2 eq.) was added to the mixture. After the mixture was warmed to room temperature, the tetrahydrofuran was removed by rotary evaporation. The pH of the solution was adjusted to about 1-2 with HCl (1 M) and the precipitated solid was collected by centrifugation. The solid was washed five times with water (2 mL) and then acetone (5 mL). The product was dried in vacuum oven at 40° C. overnight.

Example 25

((4-trifluoromethyl)benzene)phosphono chloridic acid ethyl ester

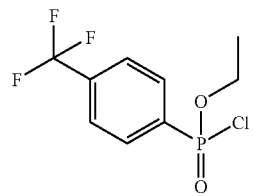

In a vial, 1-iodo-4-(trifluoromethyl)benzene (5 g, 18.4 mmol), triethyphosphite (4.16 g, 25.04 mmol) and palladium dichloride (162 mg, catalytic amount 0.05 eq) were stirred at 140° C. overnight. Distillation to remove the starting material and ethylphosphonate revealed (4-trifluoromethyl)benzenephosphonic acid diethyl ester (3.18 g, 61.3% yield), which was used in the next step. In a round bottom flask, under nitrogen atmosphere and at room temperature, 14 mL of neat oxalyl chloride was added slowly to 4-trifluoromethyl)benzenephosphonic acid diethyl ester (3.18 g) while stirring. The reaction mixture was stirred for several days. Reaction progress was monitored by $^{31}$P NMR. When conversion reached 75%, the volatiles were removed under vacuum and hexane was added to wash away the remaining oxalyl chloride to yield the desired product. This crude material (3 g, 97% yield) was taken directly to the next step.

Example 26

((4-trifluoromethylphenyl)ethoxyphosphinyl)methylphosphonic acid diethyl ester

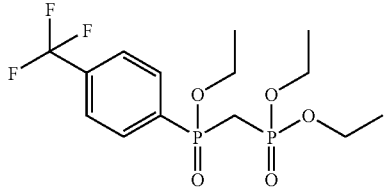

In a 2-neck round-bottomed flask, under a $N_2$ atmosphere, methylphosphonic acid diethyl ester (4 g, 22.2 mmol) was dissolved in 25 mL of anhydrous THF. This stirred solution was cooled in an acetone/dry ice bath to −72° C. A 2.5 M solution of n-butyl lithium in hexanes (10 mL) was added slowly, keeping the temperature below −60° C. The reaction mixture was left to stir for 45 minutes after the completion of the addition, and ((4-trifluoromethyl)benzene)phosphono chloridic acid ethyl ester was added slowly at −72° C. The reaction was left to stir in acetone/dry ice bath overnight. The mixture was quenched by the addition of an aqueous solution of ammonium chloride, and extracted with ethyl acetate. The organic layer was separated and concentrated in-vacuo to give 3 g of crude product. Purification by flash column chromatography (silica, ethyl acetate/methanol=2-5%) gave the desired product pure and in moderate yield (2 g, 44%).

Example 27

((4-trifluoromethylphenyl)hydroxyphosphinyl)methylphosphonic acid trisodium salt

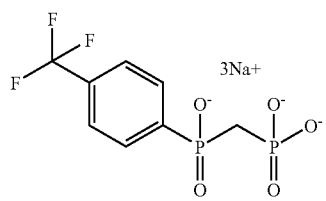

In a 8-mL vial ((4-trifluoromethylphenyl)ethoxyphosphinyl)methylphosphonic acid diethyl ester (0.4 g, 1 mmol) was stirred with tributylamine (1.4 mL, 6 mmol). Bromotrimethylsilane (1.2 mL, 9 mmol) was added at room temperature. The reaction was left to stir overnight. The volatiles were then removed and methanol (5 mL) was added, followed by a solution of sodium iodide (2.25 g) in acetone (40 mL). A white precipitate was collected, washed several times with acetone and dried in high vacuum oven. (0.3 g, 81% yield). $^1$H NMR (400 MHz, $D_2O$) δ 2.3 (dd, 2H), 7.8-8 (m, 4H). $^{31}$P NMR (400 MHz, $D_2O$) δ 14 and 27.

Example 28

Phosphate Transporter Inhibition In Vitro Testing

The following example outlines the procedures required for in vitro measurement of the inhibition of phosphate uptake by rabbit intestinal Brush Border Membrane Vesicles (BBMV).

Buffer Solution Preparation

| | 300 MET | 50 mL |
|---|---|---|
| | 300 mM mannitol | 2.73 g |
| | 5 mM EGTA | 117 mg |
| | 12 mM Tris base | 73 mg |
| | pH 7.1 (w/HCl) | |
| | 60 MET | 250 mL |
| | 60 mM mannitol | 2.73 g |
| | 5 mM EGTA | 585 mg |
| | 12 mM Tris base | 363 mg |
| | pH 7.1 (w/ HCl) | |
| | Na Uptake buffer | 50 mL |
| | 100 mM NaCl | 292 mg |
| | 50 mM HEPES | 596 mg |
| | 100 mM mannitol | 911 mg |
| | 100 uM $KH_2PO_4$ | 50 mL 0.1 M stock |
| | pH 7.4 (w/NaOH) | |
| | STOP buffer | 1000 mL |
| | 100 mM mannitol | 18.22 g |
| | 20 mM HEPES:Tris | 20 mL total of 1 M stocks |
| | 20 mM $MgSO_4$ | 4.93 g |
| | 100 mM choline Cl | 13.96 g |
| | 5 mM $KH_2PO_4$ | 681 mg |
| | 280 MH | 250 mL |
| | 280 mM mannitol | 12.75 g |
| | 20 mM HEPES | 5 mL of 1 M stock |
| | pH 7.4 (w/ KOH) | |
| | K Uptake buffer | 50 mL |
| | 100 mM KCl | 373 mg |
| | 50 mM HEPES | 596 mg |
| | 100 mM mannitol | 911 mg |
| | 100 mM $KH_2PO_4$ | 50 mL 0.1 M stock |
| | PH 7.4 (w/ KOH) | |

BBMV Isolation

Rabbit Intestinal Brush Border Membrane Vesicles (BBMV) were isolated from mucosal scrapings of the upper small intestine (duodenum) of male New Zealand White rabbits. The scrapings were divided into 2 g aliquots in cryopreservation vials, frozen in liquid nitrogen, and stored at −80° C.

The following procedure was performed for each 2 g sample of BBMV mucosal scraping. Buffer volumes and container sizes were adjusted appropriately for the number of 2 g samples used. The entire preparation was performed on ice, unless otherwise stated.

Mucosal scrapings (2 g per tube) were thawed in a 37° C. water bath for 3 minutes and then placed on ice. The scrapings were suspended with a total of 7.5 mL of 300 MET, and transferred to a 250 mL Corning tube on ice. To the suspension was added 30 mL cold (4° C.) deionized water ($dH_2O$). The suspension was homogenized with a tissue homogenizer (Polytron) on high speed for two minutes. A stir bar and $MgCl_2$ (81.3 mg) were added. The suspension was mixed well by inverting the closed tube. The suspension was stirred on ice, ensuring that a good vortex is achieved with the stir bar, for 40 minutes. The suspension was transferred to a chilled centrifuge tube and spun at 4000×g for 15 minutes. The supernatant was transferred to a new chilled centrifuge tube and spun at 32000×g for 30 minutes. The supernatant was discarded and the pellet was re-suspended with 34 mL cold 60 MET. The suspension was homogenized with a Dounce homogenizer with 8 strokes. The suspension was transferred to a fresh 250 mL Corning tube. A stir bar and 69.1 mg $MgCl_2$ were added. The suspension was stirred well on ice for 10 minutes. The suspension was transferred to a chilled centrifuge tube and spun at 4000×g for 15 minutes. The supernatant was transferred to a new chilled centrifuge tube and spun at 32000×g for 30 minutes. The supernatant was discarded. At this stage, the preparation could be continued or this pellet (P4) could be frozen in liquid nitrogen and stored at −80° C. When needed, this pellet could be allowed to thaw at room temperature for 5 minutes. Continuing the preparation, the pellet was re-suspended with 34 mL cold 280 MH. The suspension was homogenized in a Dounce homogenize with 8 strokes. The suspension was transferred to a new chilled centrifuge tube and spun at 32000×g for 30 minutes. The supernatant was discarded. To the pellet was added 500 μL 280 MH and the pellet was re-suspended very carefully with a 1 mL tuberculin syringe with a 25-gauge needle with care not to create bubbles. Once the entire pellet was suspended, the suspension was transferred to a chilled 1.5 mL microfuge tube. The suspension was evenly dispersed by bringing the suspension up into the syringe through the 25-gauge needle, and back out again eight times with care not to create bubbles. The total protein concentration was determined by performing a Bradford Protein Assay. Using that value, the BBMV were diluted with 280 MH to reach approximately 0.5-2.0 mg/mL. The solution was used as soon as possible for uptake studies.

High Throughput Screening (HTS)

$^{33}PO_4$ Uptake in Rabbit Intestinal BBMV

The following experiment was performed using a Beckman Multimek 96-tip robotic pipettor. The following outlines the preparation required to screen one 96-well plate of compounds. However, multiple plates could be screened in one experiment.

To the "Uptake Buffers" was added $^{33}PO_4$ to reach 200,000 CPM/19/μL. The buffer solutions were stored at room temperature. The following control solutions were prepared and placed into appropriate wells of a polypropylene, 96-well V-bottom plate ("Hot Stock Plate"):

a. Maximum activity (MAX)—Na Uptake buffer $^{33}PO_4$ at 200,000 CPM/19 μL b. Midline activity (MID)—MAX+100 μM $KH_2PO_4$, pH 7.4 c. Minimum activity (MIN)—K Uptake buffer+$^{33}PO^4$ at 200,000 CPM/19 μL

In the remaining wells, used for compound containing reactions, are placed MAX Control Buffer. The Hot Stock Plate was stored at room temperature. To each well of an appropriate 96-well filter plate was added approximately 200 μL Stop Buffer to pre-wet the filters for at least 15 minutes prior to assay. The "Compound Plate" was set-up by loading appropriate wells of a 96-well, polypropylene, V-bottom plate with compound solutions. This could be for testing inhibition at a single "screening" concentration, or to measure the potency of compounds by dose-response analysis at the appropriate concentrations. A "BBMV Plate" was set up by loading a 96-well, polypropylene, V-bottom plate with BBMVs at 0.5-2.0 mg/mL (prepared as described above). The BBMV Plate was kept on ice until just prior to the assay. The reaction was initiated by aspiration of the hot uptake buffers (19 μL), from the Hot Stock Plate, and the compound solutions (2 μL), from the Compound Plate, dispensing into an empty 96-well V-bottom plate (Assay Plate), then immediately aspirating the BBMVs (19 μL), from the BBMV Plate and dispensing into the same Assay Plate. The addition of the BBMVs to the assay plate marked the reaction start time. After 15 minutes, the reaction was quenched by addition of 200 μL of STOP buffer from a reservoir. The Stop Buffer was aspirated by vacuum from the wells, through the filters, of the pre-soaked filter plate using a filter plate manifold. The quenched reactions were aspirated and transferred to the filter plate under vacuum. The filters were washed two times with 200 μL STOP buffer under vacuum. The filter plate was removed, dried, and the bottom of the filter plate was sealed. To each well of the filter plate was added 50 μL of scintillant (Microscint-20). A top seal was then applied to the filter plate. The plate was incubated for approximately 20 minutes before reading for $^{33}P$ CPM on a scintillation counter (i.e., Top-Count—Packard Instruments). Percent inhibition was calculated by comparing the CPM values from compound containing wells to the MAX and MIN controls on the same plate using the following formula.

$$1-((CPM-MIN)/(MAX-MIN))$$

$IC_{50}$ values were calculated from non-linear regression analysis within an appropriate software package (i.e., Prism Graph-Pad). The results are shown below in Table 1:

TABLE 1

| Compound Structure and Number | $IC_{50}$* |
|---|---|
| <br>Compound 1 | A |

TABLE 1-continued
| Compound Structure and Number | IC$_{50}$* |
|---|---|
| 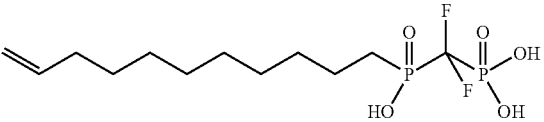<br>Compound 2 | A |
| 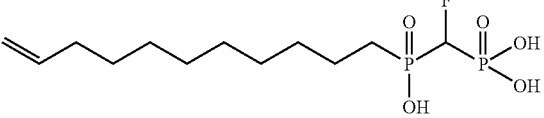<br>Compound 3 | A |
| 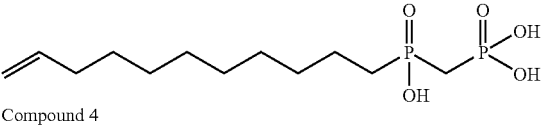<br>Compound 4 | A |
| 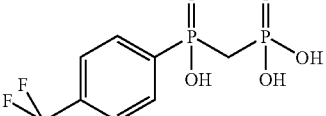<br>Compound 5 | A |
| 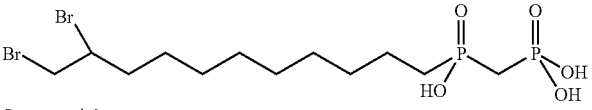<br>Compound 6 | A |
| 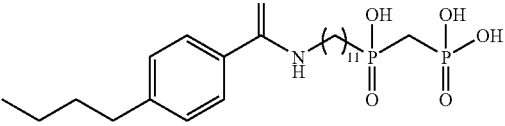<br>Compound 7 | A |
| 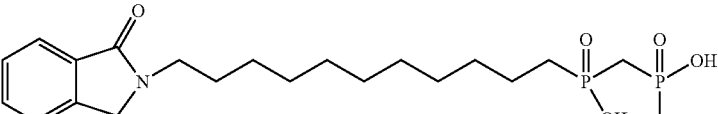<br>Compound 8 | A |
| 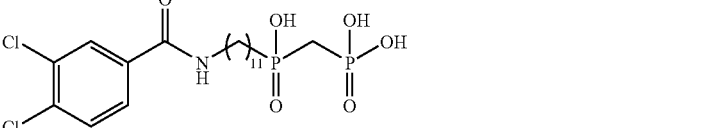<br>Compound 9 | B |
| 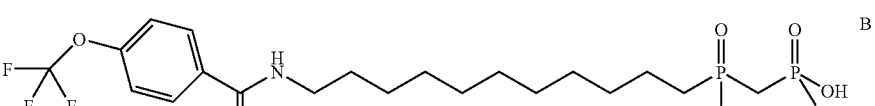<br>Compound 10 | B |

TABLE 1-continued

| Compound Structure and Number | IC$_{50}$* |
|---|---|
| Compound 11 | B |
| Compound 12 | B |
| Compound 13 | B |
| Compound 14 | B |
| Compound 15 | B |
| Compound 16 | B |
| Compound 17 | C |
| Compound 18 | C |
| Compound 19 | C |

TABLE 1-continued
| Compound Structure and Number | IC$_{50}$* |
|---|---|
| 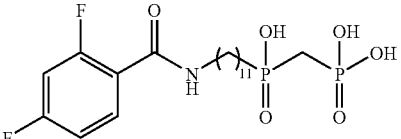<br>Compound 20 | D |
| 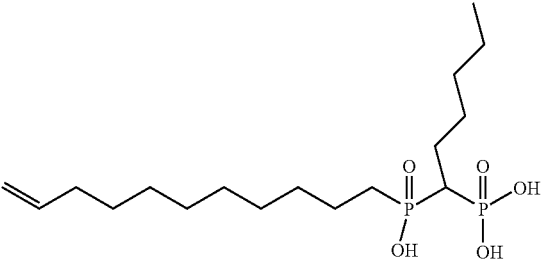<br>Compound 21 | D |
| 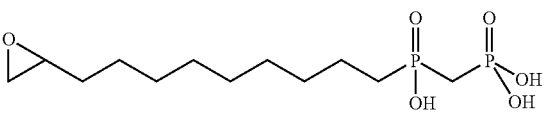<br>Compound 22 | D |
| 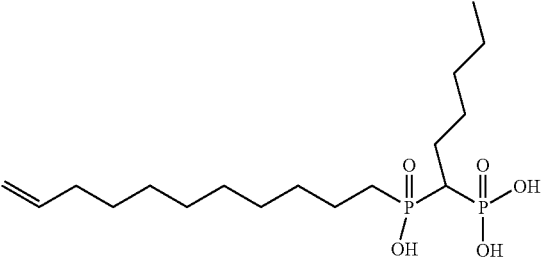<br>Compound 23 | D |
| 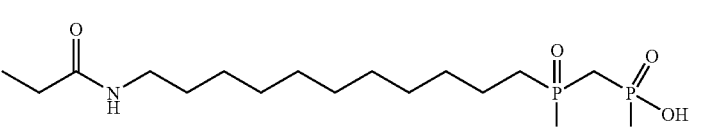<br>Compound 24 | D |
| 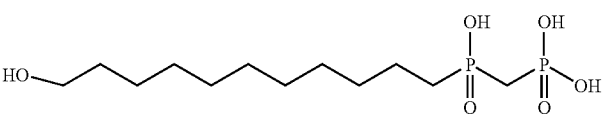<br>Compound 25 | D |

TABLE 1-continued
| Compound Structure and Number | IC$_{50}$* |
|---|---|
| 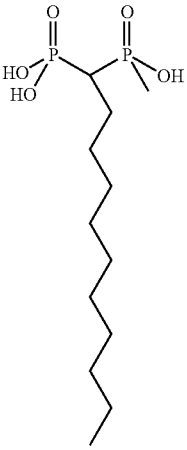<br>Compound 26 | D |
| 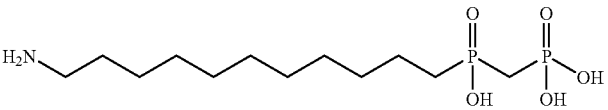<br>Compound 27 | E |
| 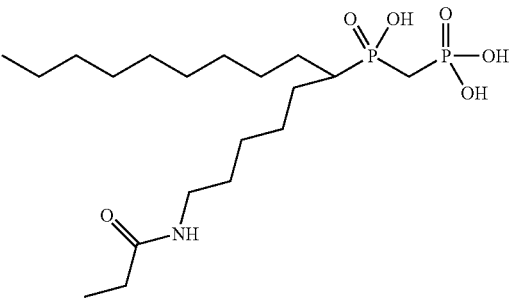<br>Compound 28 | E |
| 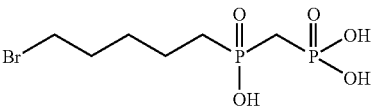<br>Compound 29 | E |
| 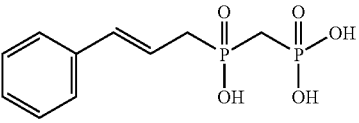<br>Compound 30 | E |
| 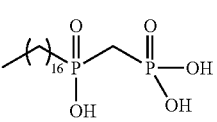<br>Compound 31 | E |

TABLE 1-continued
| Compound Structure and Number | IC$_{50}$* |
|---|---|
| 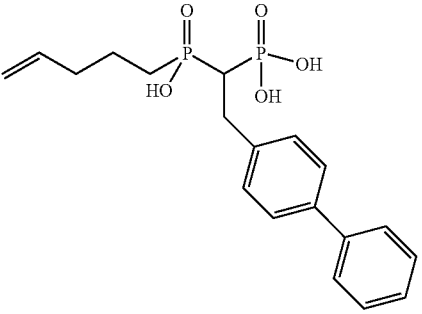<br>Compound 32 | E |
| 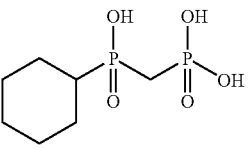<br>Compound 33 | F |
| 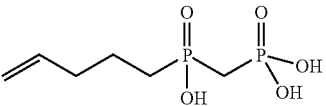<br>Compound 34 | F |
| 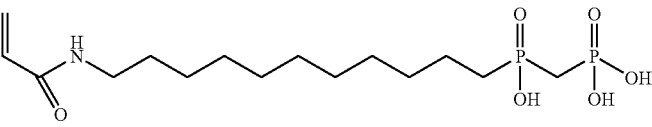<br>Compound 35 | F |
| 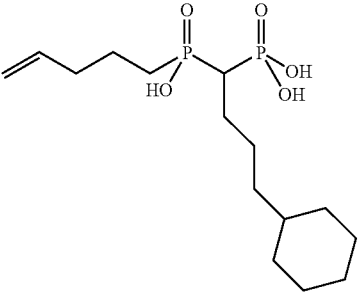<br>Compound 36 | F |
*IC$_{50}$
A - IC$_{50}$ less than 100 μM.
B - IC$_{50}$ between 100 μM and 300 μM.
C - IC$_{50}$ between 300 μM and 700 μM.
D - IC$_{50}$ between 700 μM and 1000 μM.
E - IC$_{50}$ between 1000 μM and 1600 μM.
F - IC$_{50}$ greater than 1600 μM.

While this invention has been particularly shown and described with references to preferred embodiments thereof, it will be understood by those skilled in the art that various changes in form and details may be made therein without departing from the scope of the invention encompassed by the appended claims.

What is claimed is:

1. A pharmaceutical composition comprising: i) a polyacrylate polymer comprising one or more pendant phosphinyl phosphonate groups or pharmaceutically acceptable salts thereof or esters thereof, and ii) a pharmaceutically acceptable carrier or diluent.

2. The pharmaceutical composition of claim 1, wherein the phosphinyl phosphonate groups are represented by the following structural formula:

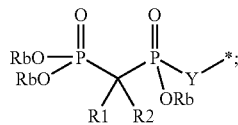

or a pharmaceutically acceptable salt or prodrug thereof, wherein:
R1 and R2 are independently —H or an electron withdrawing group;
Y is a covalent bond, a substituted methylene group or an unsubstituted methylene group; and
each Rb is independently —H, a lower alkyl group or a phosphate protecting group.

3. The pharmaceutical composition of claim 2 wherein R1 and R2 are independently —H or —F and each Rb is —H.

4. The pharmaceutical composition of claim 2 wherein the polymer comprises a hydrophilic repeat unit.

5. The pharmaceutical composition of claim 1 wherein the phosphinyl phosphonate groups are represented by the following Structural Formula:

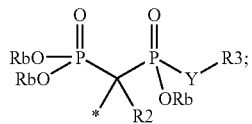

or a pharmaceutically acceptable salt or prodrug thereof, wherein:
R2 is —H or an electron withdrawing group;
R3 is a hydrocarbyl group optionally comprising one or more amine, ammonium, ether, thioether or phenylene linking groups; a substituted hydrocarbyl group optionally comprising one or more amine, ammonium, ether, thioether or phenylene linking groups; a heteroaryl group; a substituted heteroaryl group; or a phenyl group substituted with one or more groups selected from —Cl, —Br, —F, —CN, —NO$_2$, —OR$^a$, —N(R$^a$)$_2$, —COOR, —CON(R$^a$)$_2$, —COR$^a$, —S(O)R$^a$, —S(O)$_2$R$^a$, —S(O)$_2$N(R$^a$)$_2$, —NR$^a$S(O)$_2$R$^a$, —NR$^a$COR$^a$, a halogenated lower alkyl group, an aryl group, a substituted aryl group, or a halogenated alkoxy group;
Y is a covalent bond, a substituted methylene group or an unsubstituted methylene group; and
each Rb is independently —H, a lower alkyl group or a phosphate protecting group.

6. The pharmaceutical composition of claim 1 wherein the phosphinyl phosphonate groups are represented by the following Structural Formula:

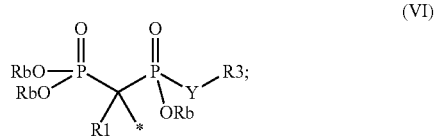

or a pharmaceutically acceptable salt or prodrug thereof, wherein:
R1 is —H or an electron withdrawing group;
R3 is a hydrocarbyl group optionally comprising one or more amine, ammonium, ether, thioether or phenylene linking groups; a substituted hydrocarbyl group optionally comprising one or more amine, ammonium, ether, thioether or phenylene linking groups;
a heteroaryl group; a substituted heteroaryl group; or a phenyl group substituted with one or more groups selected from —Cl, —Br, —F, —CN, —NO$_2$, —OR$^a$, —N(R$^a$)$_2$, —COOR, —CON(R$^a$)$_2$, —COR$^a$, —S(O)R$^a$, —S(O)$_2$R$^a$, —S(O)$_2$N(R$^a$)$_2$—NR$^a$S(O)$_2$R$^a$, —NR$^a$COR$^a$, a halogenated lower alkyl group, an aryl group, a substituted aryl group, or a halogenated alkoxy group;
Y is a covalent bond, a substituted methylene group or an unsubstituted methylene group; and
each Rb is independently —H, a lower alkyl group or a phosphate protecting group.

7. The pharmaceutical composition of claim 1 wherein the polymer comprises repeat units represented by the following structural formula:

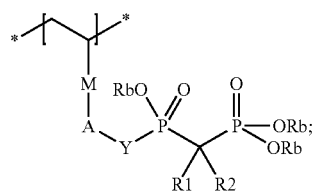

wherein:
M is —NR6-, —O—, —C(O)—, —C(O)O—, —C(O)NR6-, —NR6C(O)—, or —(CH$_2$)$_q$,- or phenylene;
A is a covalent bond or an inert spacer group;
R1 and R2 are independently —H or an electron withdrawing group;
Y is a covalent bond, a substituted methylene group or an unsubstituted methylene group;
R6 is hydrogen, an aliphatic group or a substituted lower aliphatic group;
each Rb is independently —H, a lower alkyl group or a phosphate protecting group; and
q is 0 or 1.

8. The pharmaceutical composition of claim 7 wherein R1 and R2 are independently —H or —F and Y is a covalent bond, —CH$_2$-, —CHF— or —CF$_2$-.

9. The pharmaceutical composition of claim 8 wherein A is a hydrocarbyl group optionally comprising one or more amine, ether, thioether, amide or ester linking groups.

10. The pharmaceutical composition of claim 9 wherein A is an alkylene group.

11. The pharmaceutical composition of claim 7 where the polymer is a copolymer.

12. The pharmaceutical composition of claim 11 wherein the polymer comprises a hydrophilic co-monomer.

13. A method of inhibiting phosphate transport in a subject in need of phosphate transport inhibition, said method comprising the step of administering to the subject an effective amount of a polyacrylate polymer comprising one or more pendant phosphinyl phosphonate groups or a pharmaceutically acceptable salt thereof or ester thereof.

14. The method of claim 13 wherein the subject is in need of treatment for hyperphosphotemia.

15. The method of claim 13 wherein the subject is in need of treatment for chronic renal failure.

16. The method of claim 13 wherein the subject is in need of treatment for, disorders of phosphate metabolism or impaired phosphate transport function.

17. The method of claim 13 wherein the subject is in need of treatment for hyperparathyroidism, uremic bone disease, soft tissue calcification or osteoporosis.

18. The method of claim 13 wherein the method further comprises co-administering to the subject one or more phosphate sequesterants or one or more metal ion sequestrants.

19. The method of claim 13 wherein the phosphinyl phosphonate group has the formula:

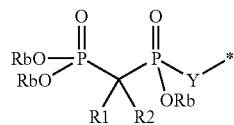

or a pharmaceutically acceptable salt or prodrug thereof, wherein:
  R1 and R2 are independently —H or an electron withdrawing group;
  Y is a covalent bond, a substituted methylene group, or an unsubstituted methylene group; and
  each Rb is independently —H, a lower alkyl group or a phosphate protecting group.

* * * * *